(12) United States Patent
Takenouchi et al.

(10) Patent No.: US 10,523,911 B2
(45) Date of Patent: Dec. 31, 2019

(54) IMAGE PICKUP SYSTEM

(71) Applicant: OLYMPUS CORPORATION, Tokyo (JP)

(72) Inventors: Yusuke Takenouchi, Hachioji (JP); Koji Kojima, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 122 days.

(21) Appl. No.: 15/581,066

(22) Filed: Apr. 28, 2017

(65) Prior Publication Data

US 2017/0230634 A1   Aug. 10, 2017

Related U.S. Application Data

(63) Continuation of application No. PCT/JP2015/081307, filed on Nov. 6, 2015.

(30) Foreign Application Priority Data

Nov. 7, 2014 (JP) ................................. 2014-227335

(51) Int. Cl.
*H04N 13/00* (2018.01)
*A61B 1/00* (2006.01)
(Continued)

(52) U.S. Cl.
CPC ....... *H04N 13/122* (2018.05); *A61B 1/00193* (2013.01); *A61B 1/05* (2013.01); (Continued)

(58) Field of Classification Search
CPC ..... G02B 23/2484; G02B 23/24; G02B 23/26
See application file for complete search history.

(56) References Cited

U.S. PATENT DOCUMENTS 5,860,912 A * 1/1999 Chiba ................ A61B 1/00059
600/111
6,063,023 A   5/2000 Sakiyama et al.

FOREIGN PATENT DOCUMENTS

JP   H08-029701 A   2/1996
JP   H10-248806 A   9/1998
(Continued)

OTHER PUBLICATIONS

International Search Report dated Feb. 2, 2016 issued in PCT/JP2015/081307.

*Primary Examiner* — Anand S Rao
*Assistant Examiner* — Tyler B Edwards
(74) *Attorney, Agent, or Firm* — Scully, Scott, Murphy & Presser, P.C.

(57) ABSTRACT

An image pickup system includes: an image pickup section including a first image pickup device outputting a first image pickup signal, and a second image pickup device outputting a second image pickup signal; a processor that performs signal processing on image pickup signals; and a memory section holding a difference correction parameter, the difference correction parameter indicating difference of image characteristics derived from sensitivity of each image pickup device, in image pickup signals outputted from the first image pickup device and the second image pickup device; and a correction processing section performing correction processing on at least one of the first image pickup signal and the second image pickup signal, based on the difference correction parameter.

10 Claims, 12 Drawing Sheets

(51) Int. Cl.
  *G02B 23/24* (2006.01)
  *H04N 5/235* (2006.01)
  *H04N 1/60* (2006.01)
  *A61B 1/05* (2006.01)
  *H04N 13/122* (2018.01)
  *H04N 13/204* (2018.01)
  *H04N 13/254* (2018.01)

(52) U.S. Cl.
  CPC ....... *G02B 23/2484* (2013.01); *H04N 1/6027* (2013.01); *H04N 1/6077* (2013.01); *H04N 5/2351* (2013.01); *H04N 13/204* (2018.05); *H04N 13/254* (2018.05)

(56) References Cited

FOREIGN PATENT DOCUMENTS

| JP | 2007-044153 | A |   | 2/2007 |
| JP | 2007044153  | A | * | 2/2007 |
| JP | 4955840     | B2|   | 6/2012 |
| JP | 2012-134875 | A |   | 7/2012 |
| JP | 2012134875  | A | * | 7/2012 |

\* cited by examiner

IMAGE PICKUP SYSTEM

CROSS REFERENCE TO RELATED APPLICATION

This application is a continuation application of PCT/JP2015/081307 filed on Nov. 6, 2015 and claims benefit of Japanese Application No. 2014-227335 filed in Japan on Nov. 7, 2014, the entire contents of which are incorporated herein by this reference.

BACKGROUND OF THE INVENTION

1. Field of the Invention

The present invention relates to an image pickup system, and in particular to an image pickup system that includes two image pickup optical systems and acquires two picked-up images.

2. Description of the Related Art

In related art, an image pickup system that acquires two picked-up images having parallax with respect to each other, that is, an image pickup system that generates a stereoscopic image with use of the two picked-up images having parallax, is known.

For example, Japanese Patent No. 4955840 discloses a stereoscopic endoscope that generates a stereoscopic image with use of two picked-up images having parallax in order to allow stereoscopic observation of a fine operative site in a body cavity in surgery. The stereoscopic endoscope includes a pair of right and left observation optical systems and a pair of right and left image pickup sections corresponding to the observation optical systems.

SUMMARY OF THE INVENTION

An image pickup system according to an aspect of the present invention includes: an image pickup section including a first image pickup device capable of picking up an optical image of an object and outputting the optical image as a first image pickup signal, and a second image pickup device capable of picking up an optical image of the object and outputting the optical image as a second image pickup signal having parallax with respect to the first image pickup signal; a processor connected to the image pickup section, the processor performing signal processing on the first image pickup signal and the second image pickup signal; a memory section provided in the image pickup section, the memory section holding a difference correction parameter, the difference correction parameter indicating a difference of image characteristics derived from sensitivity of each image pickup device, in image pickup signals outputted from the first image pickup device and the second image pickup device; and a correction processing section provided in the processor, the correction processing section performing correction processing on at least one of the first image pickup signal and the second image pickup signal, based on the difference correction parameter, to cause image characteristics for each pixel expressed by one of the first image pickup signal and the second image pickup signal to become equal to image characteristics for each pixel expressed by another image pickup signal.

An image pickup system according to another aspect of the present invention includes a processor that performs signal processing on a first image pickup signal and a second image pickup signal, the processor being connectable to an image pickup section that includes a first image pickup device capable of picking up an optical image of an object and outputting the optical image as the first image pickup signal, a second image pickup device capable of picking up an optical image of the object and outputting the optical image as the second image pickup signal having parallax with respect to the first image pickup signal, and a memory section holding a difference correction parameter, the difference correction parameter indicating difference of image characteristics derived from sensitivity of each image pickup device, in image pickup signals outputted from the first image pickup device and the second image pickup device; and a correction processing section provided in the processor, the correction processing section performing correction processing on at least one of the first image pickup signal and the second image pickup signal, based on the difference correction parameter, to cause image characteristics for each pixel expressed by one of the first image pickup signal and the second image pickup signal to become equal to image characteristics for each pixel expressed by another image pickup signal.

DETAILED DESCRIPTION OF THE PREFERRED EMBODIMENTS

Figure 1:
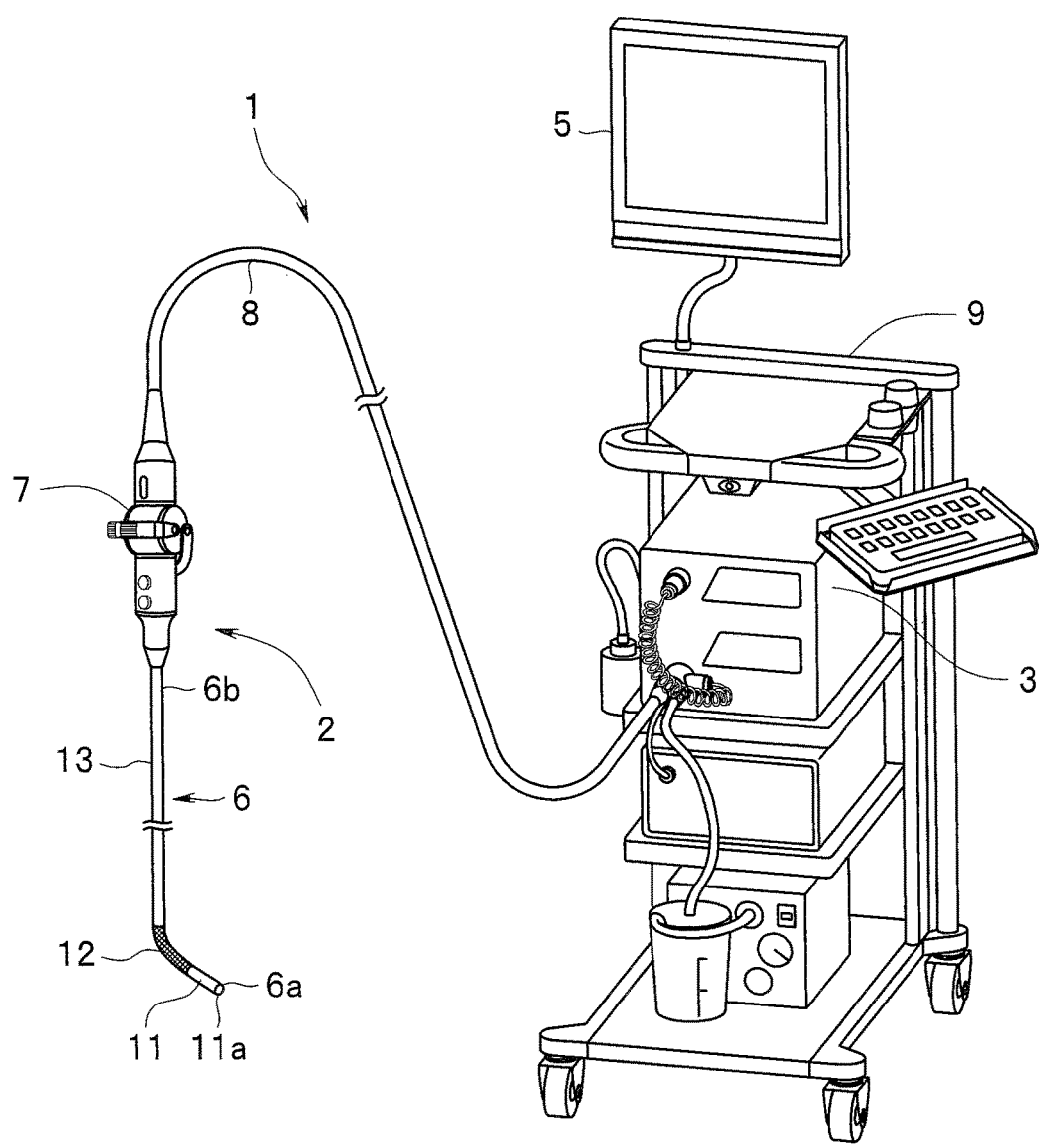
FIG. 1 is an appearance perspective view illustrating an entire configuration of an endoscope system according to a first embodiment of the present invention.

Preferred embodiments of the present invention are described below with reference to drawings. Note that, in the diagrams used for the following description, a scale is varied for each of components in order to illustrate the components with respective recognizable sizes in the drawings. The present invention is not limited only to the number of components illustrated in the drawings, shapes of the respective components, a ratio of the size between the components, and relative positional relationship between the components.
(First Embodiment)

Figure 2:
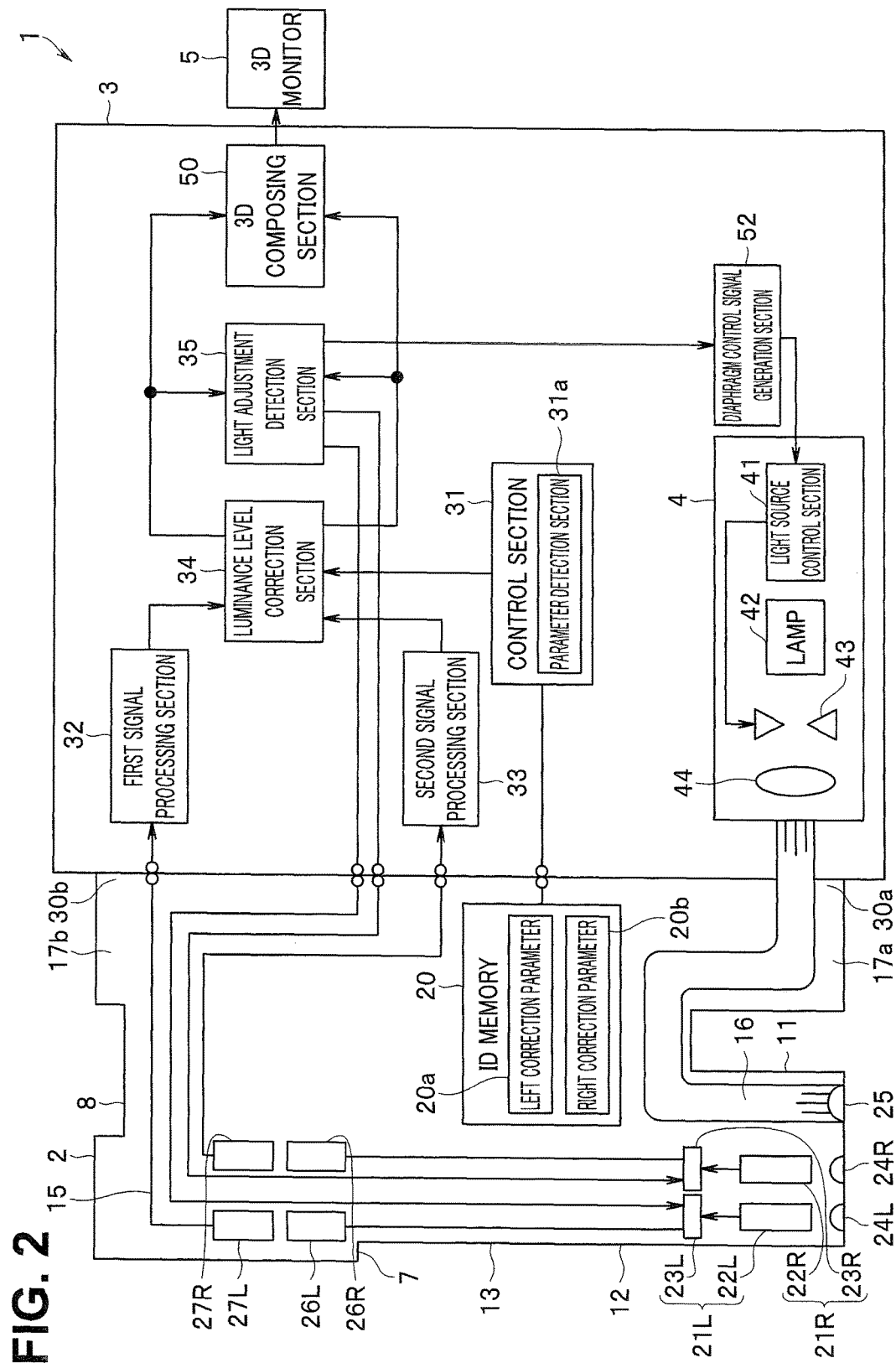
FIG. 2 is a block diagram illustrating a configuration of the endoscope system according to the first embodiment.
Figure 3:
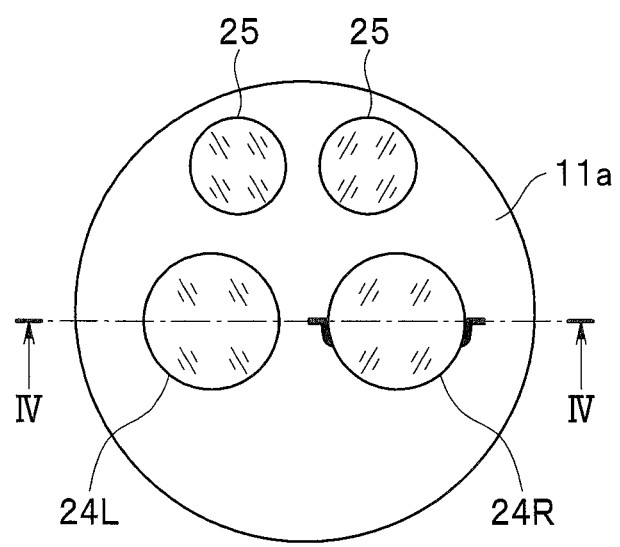
FIG. 3 is a front view of a distal end portion of an insertion section of an endoscope in the endoscope system according to the first embodiment.
Figure 4:
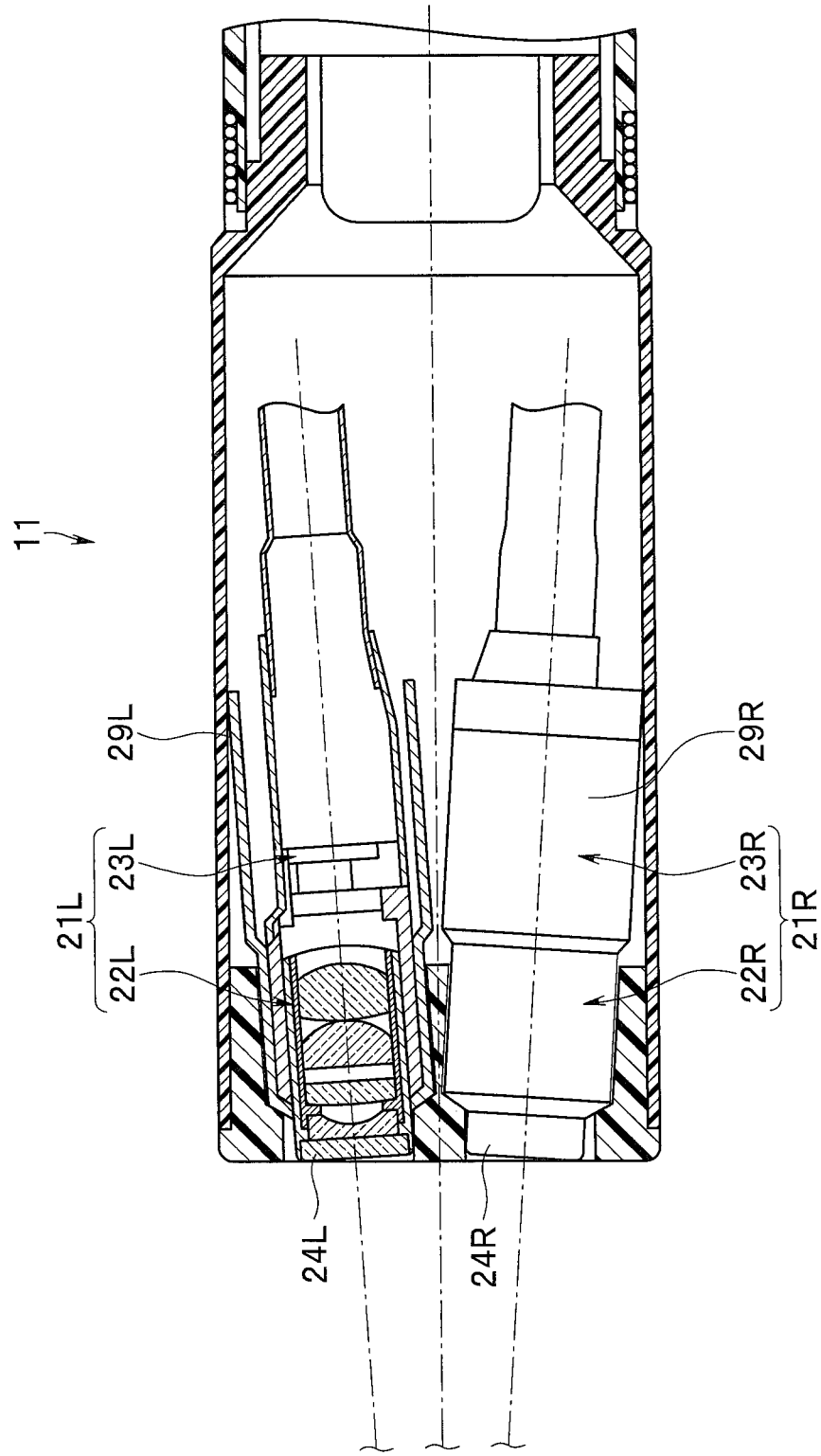
FIG. 4 is a cross-sectional diagram of the distal end portion of the insertion section of the endoscope in the endoscope system according to the first embodiment.

A configuration of an endoscope system according to a first embodiment is described with reference to FIG. 1 to FIG. 4. FIG. 1 is an appearance perspective view illustrating an entire configuration of the endoscope system according to the first embodiment of the present invention. FIG. 2 is a block diagram illustrating a configuration of the endoscope system according to the first embodiment. FIG. 3 is a font view of a distal end portion of an insertion section of an endoscope in the endoscope system according to the first embodiment. FIG. 4 is a cross-sectional diagram of the distal end portion of the insertion section of the endoscope in the endoscope system according to the first embodiment.

As illustrated in FIG. 1, an endoscope system 1 according to the first embodiment of the present invention includes, as a main section, a stereoscopic endoscope 2, a processor 3, and a monitor 5. The stereoscopic endoscope 2 serves as a so-called 3D endoscope that generates a stereoscopic image with use of two image pickup units having parallax with respect to each other. The processor 3 is connected with the detachable stereoscopic endoscope 2, performs predetermined signal processing on image pickup signals respectively provided from the image pickup units, and includes a light source section that supplies illumination light to the stereoscopic endoscope 2. The monitor 5 is a display apparatus that displays, as an endoscope image, an image signal generated by the processor 3.

Note that the endoscope system 1 according to the present embodiment is mounted on a cart 9, together with various kinds of medical instruments including the processor 3, for example, apparatuses such as an electric scalpel device, a pneumoperitoneum apparatus, and a video recorder, and a gas cylinder filled with carbon dioxide, in an operating room.

In the present embodiment, the stereoscopic endoscope 2 is a rigid endoscope applied to, for example, intraperitoneal procedure that enables stereoscopic observation of an operative site in a body cavity. The stereoscopic endoscope 2 includes a rigid insertion section 6, an operation section 7, and a universal cord 8. The insertion section 6 is inserted into a body cavity and has a length applied to the intraperitoneal procedure. The operation section 7 is held by an operator to perform various operations of the stereoscopic endoscope 2. The universal cord 8 is extended from the operation section 7 and is connected to the processor 3.

The insertion section 6 includes a distal end rigid portion 11, a bending portion 12, and a rigid portion 13 that are coupled with one another in order from a distal end portion 6a side toward a proximal end portion 6b. In other words, a proximal end portion of the distal end rigid portion 11 is coupled with a distal end portion of the bending portion 12, and a proximal end portion of the bending portion 12 is coupled with a distal end portion of the rigid portion 13. In addition, the rigid portion 13 is an elongated rigid tube, and a proximal end portion of the rigid portion 13 is coupled, as the proximal end portion 6b of the insertion section 6, with the operation section 7.

In addition, as illustrated in FIG. 2, FIG. 3, and FIG. 4, a left image pickup unit 21L for a left image (a left eye) and a right image pickup unit 21R for a right image (a right eye) are provided on the distal end rigid portion 11 of the insertion section 6 in order to enable stereoscopic observation of the operative site.

The left image pickup unit 21L is configured of an image pickup optical system 22L for a left image (a left eye) and an image pickup device 23L for a left image (a left eye). The right image pickup unit 21R is configured of an image pickup optical system 22R for a right image (a right eye) and an image pickup device 23R for a right image (a right eye).

Further, as illustrated in FIG. 4, each of the image pickup optical system 22L for the left image and the image pickup optical system 22R for the right image is configured of an objective lens that is used to observe the operative site, and an image forming lens that forms an image of the operative site observed through the objective lens.

Further, the image pickup device 23L for the left image and the image pickup device 23R for the right image are provided at respective image forming positions of the image forming lenses of the image pickup optical system 22L and the image pickup optical system 22R. Each of the image pickup device 23L for the left image and the image pickup device 23R for the right image is configured of, for example, a CCD image sensor, and photoelectrically converts an image (the operative site) that has passed through the corresponding objective lens of the image pickup optical system 22L or the image pickup optical system 22R and has formed by the corresponding image forming lens, to generate a predetermined image signal.

Moreover, correlated double sampling circuits (hereinafter, referred to as CDS circuits) 26L and 26R and analog-to-digital conversion circuits (hereinafter, referred to as A/D conversion circuits) 27L and 27R are respectively provided in the rear stages of the image pickup device 23L for the left image and the image pickup device 23R for the right image.

The image pickup device 23L for the left image and the image pickup device 23R for the right image photoelectrically convert an object image formed on an image pickup surface to respectively provide the converted object image to the CDS circuits 26L and 26R. The CDS circuits 26L and 26R perform correlated double sampling processing on an image pickup signal to respectively provide the processed signals to the A/D conversion circuits 27L and 27R. The A/D conversion circuits 27L and 27R respectively convert the image pickup signals from analog signals into digital signals, and respectively provide the converted signals to the processor 3.

On the other hand, various kinds of cables 15 such as signal lines relating to the image pickup device 23L for the left image and the image pickup device 23R for the right image pass through the inside of the insertion section 6, the operation section 7, and the universal cord 8, and are connected to the processor 3. In addition, a light guide cable 16 that transmits the illumination light from the light source section of the processor 3 is inserted into the insertion section 6, the operation section 7, and the universal cord 8.

A light source connector 17a that is an end portion of the light guide cable 16 is disposed on the proximal end side of the universal cord 8, and is detachably connected to a light source connector part 30a of the processor 3. On the other hand, a signal connector 17b that is an end portion of the signal cable 15 is branched from the light source connector 17a and provided, and is detachably connected to a signal connector part 30b of the processor 3.

An ID memory 20 serving as a memory section that holds individual information for each stereoscopic endoscope 2 is provided in the signal connector 30b. In the first embodiment, information relating to sensitivity characteristics of the image pickup device 23L for the left image and the image pickup device 23R for the right image that are mounted on the stereoscopic endoscope 2 is held by the ID memory 20.

In other words, as mentioned above, a solid-state image pickup device such as a CCD typically has individual sensitivity characteristics depending on variation of the device itself or the like. The image pickup device 23L for the left image and the image pickup device 23R for the right image that are mounted on the stereoscopic endoscope 2 may also have different sensitivity characteristics from each other.

Further, the sensitivity characteristics difference between the two image pickup devices influence the image pickup signals relating to the respective image pickup devices. In the first embodiment, to correct influence to the image pickup signals, respective correction parameters relating to the sensitivity characteristics of the image pickup device 23L for the left image and the image pickup device 23R for the right image are held by the ID memory 20 as a left correction parameter 20a and a right correction parameter 20b. Note that the detail of the correction parameters is described later.

With reference to FIG. 3 again, an illumination window 25 is provided at a position of a distal end surface 11a of the distal end rigid portion 11 of the insertion section 6. The position faces a distal end surface of the light guide cable 16. Note that, in the present embodiment, two light guide cables 16 are provided, and two illumination windows 25 are also provided.

The light source connector 17a is connected to the light source connector part 30a of the processor 3, and illumination light that has been emitted from a light source section 4 installed in the processor 3 is transmitted by the light guide cable 16. Then, the illumination light is outputted from the illumination window 25 provided on the distal end surface 11a of the distal end rigid portion 11 to face the distal end surface of the light guide cable 16.

On the other hand, two observation windows 24L and 24R are provided on the distal end surface 11a of the distal end rigid portion 11 to be adjacent to the illumination windows 25, and receive an optical image of the illuminated object such as an affected part. Note that the observation windows 24L and 24R are disposed at positions respectively facing the image pickup optical system 22L and the image pickup optical system 22R mentioned above.

Further, as illustrated in FIG. 4, the stereoscopic endoscope 2 includes a left housing portion 29L that houses the left image pickup unit 21L and a right housing portion 29R that houses the right image pickup unit 21R. Note that the housing portion 29L is provided separately from the housing portion 29R.

In addition, a CCD image sensor is adopted as the image pickup device 23L for the left image and the image pickup device 23R for the right image in the present embodiment; however, the image pickup device is not limited to the CCD image sensor, and, for example, an image sensor such as a CMOS may be adopted.

Next, the processor 3 in the endoscope system according to the first embodiment is described in detail.

As illustrated in FIG. 2, the processor 3 according to the present embodiment includes an unillustrated power supply circuit, an unillustrated CCD drive circuit, a control section 31, a first signal processing section 32, and a second signal processing section 33. The power supply circuit generates a plurality of power supply voltages necessary for operation of the image pickup devices and other components. The CCD drive circuit drives the image pickup device 23L for the left image and the image pickup device 23R for the right image in the stereoscopic endoscope 2. The control section 31 controls various kinds of circuits in the processor 3. The first signal processing section 32 receives one of the two image pickup signals in the stereoscopic endoscope 2 (hereinafter, referred to as a first image pickup signal), and performs predetermined signal processing on the first image pickup signal under the control of the control section 31. The second signal processing section 33 receives an image pickup signal (hereinafter, referred to as a second image pickup signal), and performs predetermined signal processing on the second image pickup signal under the control of the control section 31. The first image pickup signal has been generated by the image pickup device 23L for the left image and passed through the CDS circuit 26L and the A/D conversion circuit 27L. The second image pickup signal has been generated by the image pickup device 23R for the right image and passed through the CDS circuit 26R and the A/D conversion circuit 27R.

The control section 31 controls the various kinds of circuits in the processor 3 as mentioned above, and includes a parameter detection section 31a that detects predetermined parameter information held by the ID memory 20 in the signal connector 30b of the stereoscopic endoscope 2.

In other words, the parameter detection section 31a detects the left correction parameter 20a and the right correction parameter 20b that are held by the ID memory 20 in the signal connector 30b when the stereoscopic endoscope 2 is connected to the processor 3.

Further, the first signal processing section 32 and the second signal processing section 33 each include well-known signal processing sections such as an automatic gain control circuit (an AGC circuit), a white balance circuit, a gamma correction circuit, a magnification reduction circuit, and a contour enhancement circuit, thereby respectively appropriately performing the predetermined signal processing on the image pickup signals provided from the image pickup device 23L for the left image and the image pickup device 23R for the right image.

The processor 3 also includes a luminance level correction section 34 that performs, under the control of the control section 31, luminance level correction processing on the image pickup signals that have been subjected to the predetermined processing in the first signal processing section 32 and the second signal processing section 33. The luminance level correction section 34 is connected to respective output ends of the first signal processing section 32 and the second signal processing section 33.

The luminance level correction section 34 performs, under the control of the control section 31, correction processing on the first image pickup signal and the second image pickup signal that are respective output signals of the first signal processing section 32 and the second signal processing section 33 such that the processed image pickup signals have respective predetermined luminance levels. The luminance level correction section 34 performs the correction processing based on the left correction parameter 20a and the right correction parameter 20b that are detected by the parameter detection section 31a of the control section 31. The luminance level correction section 34 then outputs the processed image pickup signals to the following stage.

<Correction Parameter in First Embodiment>

The correction parameters in the first embodiment are described now.

As mentioned above, a solid-state image pickup device such as a CCD typically has individual sensitivity characteristics depending on variation of the device itself or the like. In the present embodiment, the left correction parameter 20a and the right correction parameter 20b are information to correct, on the stereoscopic endoscope side, difference of the sensitivity characteristics between the two right and left solid-state image pickup devices.

In other words, the left correction parameter 20a is a first correction parameter that causes the luminance level correction section 34 to correct the first image pickup signal such that the luminance level of the image expressed by the first image pickup signal relating to the image pickup device 23L for the left image becomes a predetermined luminance value, according to the sensitivity characteristics derived from physical characteristics of the image pickup device 23L for the left image itself.

On the other hand, the right correction parameter 20b is a second correction parameter that causes the luminance level correction section 34 to correct the second image pickup signal such that the luminance level of the image expressed by the second image pickup signal relating to the image pickup device 23R for the right image becomes a predetermined luminance value, according to the sensitivity characteristics derived from physical characteristics of the image pickup device 23R for the right image itself.

In other words, the left correction parameter 20a and the right correction parameter 20b are luminance level correction information used to correct a luminance level of each pixel in the first image pickup signal and the second image pickup signal.

Further, in the present embodiment, the luminance level correction section 34 performs correction processing such that the luminance level of the image expressed by the first image pickup signal becomes equal to the luminance level of the image expressed by the second image pickup signal, based on the left correction parameter 20a and the right correction parameter 20b.

In other words, the luminance level correction section 34 performs the above-described predetermined correction processing based on the correction parameters such that the first image pickup signal relating to the image pickup device 23L for the left image and the second image pickup signal relating to the image pickup device 23R for the right image are outputted as signals that has been processed with equivalent sensitivity characteristics without being influenced by the above-described variation of the solid-state image pickup device and the like.

Accordingly, the first corrected image pickup signal and the second corrected image pickup signal that are output signals subjected to the correction processing by the luminance level correction section 34 are regarded as two image pickup signals that are picked up by the two solid-state image pickup devices that have substantially uniformized sensitivity characteristics.

With reference to FIG. 2 again, one light adjustment detection section 35 and a 3D composing section 50 are provided in the rear stage of the luminance level correction section 34 of the processor 3. The light adjustment detection section 35 performs predetermined light adjustment detection, based on the first corrected image pickup signal and the second corrected image pickup signal that are output signals of the luminance level correction section 34. The 3D composing section 50 composes the first corrected image pickup signal and the second corrected image pickup signal to generate a predetermined 3D image signal.

The light adjustment detection section 35 performs the well-known light adjustment detection function. The light adjustment detection section 35 includes a photometry section that measures luminance of the first corrected image pickup signal (the signal relating to the image pickup device 23L for the left image) and luminance of the second corrected image pickup signal (the signal relating to the image pickup device 23R for the right image), and outputs information signals relating to the respective measured luminance values.

Moreover, the light adjustment detection section 35 includes an exposure time control section that controls an exposure time of the image pickup device 23L for the left image and the image pickup device 23R for the right image, according to the luminance values measured by the photometry section. The exposure time control section generates, according to the measured luminance values, control signals for electronic shutter control of the image pickup device 23L for the left image and the image pickup device 23R for the right image, and transmits the control signals to the image pickup device 23L for the left image and the image pickup device 23R for the right image.

Note that, as mentioned above, since the first corrected image pickup signal and the second corrected image pickup signal are regarded as the two image pickup signals picked up by the two solid-state image pickup devices having substantially uniformized sensitivity characteristics, it is not necessary to provide the light adjustment detection section 35 for each of the two image pickup signals, and only one light adjustment detection section 35 is sufficient in the present embodiment.

The processor 3 further includes a diaphragm control signal generation section 52 that generates a diaphragm control signal to control a diaphragm of the light source section 4, according to the information signals relating to the measured luminance values provided from the light adjustment detection section 35.

In addition, in the present embodiment, the processor 3 includes therein the light source section 4 that emits the illumination light to the light guide cable 16 in order to supply the illumination light to the stereoscopic endoscope 2.

The light source section 4 includes a lamp 42, a diaphragm 43, a lens 44, and a light source control section 41. Illumination light from the lamp 42 is outputted toward the lens 44 through the diaphragm 43 that is controlled by the light source control section 41. In addition, the lens 44 condenses light on the proximal end portion of the light guide cable 16.

Further, the light condensed on the proximal end portion of the light guide cable 16 is outputted from the distal end portion of the light guide cable 16 after being transmitted through the light guide cable 16, as illumination light to be supplied to the stereoscopic endoscope 2.

The light source control section 41 controls the diaphragm 43, based on the diaphragm control signal generated by the diaphragm control signal generation section 52.

<Action of First Embodiment>

Next, action of the endoscope system according to the first embodiment is described.

When the stereoscopic endoscope 2 is connected to the processor 3, the control section 31 detects, through the parameter detection section 31a, the left correction parameter 20a and the right correction parameter 20b that are held by the ID memory 20.

Thereafter, the luminance level correction section 34 performs, under the control of the control section 31, the correction processing with the corresponding luminance levels on the first image pickup signal and the second image pickup signal that are output signals of the first signal processing section 32 and the second signal processing section 33, based on the left correction parameter 20*a* and the right correction parameter 20*b* that are detected by the parameter detection section 31*a* of the control section 31.

Further, the luminance level correction section 34 outputs the first image pickup signal and the second image pickup signal both subjected to the correction processing, as the first corrected image pickup signal and the second corrected image pickup signal, respectively.

Thereafter, the light adjustment detection section 35 performs the predetermined light adjustment detection processing on the first corrected image pickup signal and the second corrected image pickup signal, and measures the luminance of the corrected image pickup signals to transmit information signals relating to the respective measured luminance values to the diaphragm control signal generation section 52.

Further, the light adjustment detection section 35 generates control signals for electronic shutter control of the image pickup device 23L for the left image and the image pickup device 23R for the right image, according to the measured luminance values, and transmits the control signals to the image pickup device 23L for the left image and the image pickup device 23R for the right image.

On the other hand, the 3D composing section 50 composes the first corrected image pickup signal and the second corrected image pickup signal to generate a predetermined 3D image signal, and transmits the composed 3D image signal to the 3D monitor 50.

As described above, according to the present embodiment, in the endoscope system including the stereoscopic endoscope mounted with the two right and left solid-state image pickup devices, the correction parameters that are the information used to correct the difference of the sensitivity characteristics between the two right and left solid-state image pickup devices are held on the stereoscopic endoscope side, and the predetermined correction processing is performed on the two right and left image pickup signals to correct the difference of the sensitivity characteristics between the two right and left solid-state image pickup devices, on the processor side connected to the stereoscopic endoscope, based on the correction parameters.

Therefore, even if difference of the sensitivity characteristics occurs between the two solid-state image pickup devices to be mounted on the endoscope due to variation or other causes, it is possible to correct the difference of the sensitivity characteristics between the two right and left solid-state image pickup devices on the processor 3 side. Therefore, it is not necessary to provide the light adjustment detection section 35 for each of the two image pickup signals, and only one light adjustment detection section 35 is sufficient, which results in reduction of the cost.

(Second Embodiment)

Next, a second embodiment of the present invention is described.

As mentioned above, in the endoscope system according to the first embodiment, the stereoscopic endoscope side holds and uses, as the two correction parameters to correct the difference of the sensitivity characteristics between the two right and left solid-state image pickup devices, the first correction parameter (the left correction parameter 20*a*) for correction of the first image pickup signal relating to the image pickup device 23L for the left image and the second correction parameter (the right correction parameter 20*b*) for correction of the second image pickup signal relating to the image pickup device 23R for the right image.

In contrast, in an endoscope system according to the second embodiment, the stereoscopic endoscope side holds and uses one correction parameter relating to the difference information of the sensitivity characteristics between the two right and left solid-state image pickup devices, while the two correction parameters (the left correction parameter 20*a* and the right correction parameter 20*b*) respectively used for correction of the two right and left image pickup signals relating to the two left and right solid-state image pickup devices are prepared in the first embodiment, although the correction parameter of the second embodiment is similar to the correction parameters of the first embodiment in that the correction parameter is used to correct the difference of the sensitivity characteristics between the two right and left solid-state image pickup devices.

Figure 5:
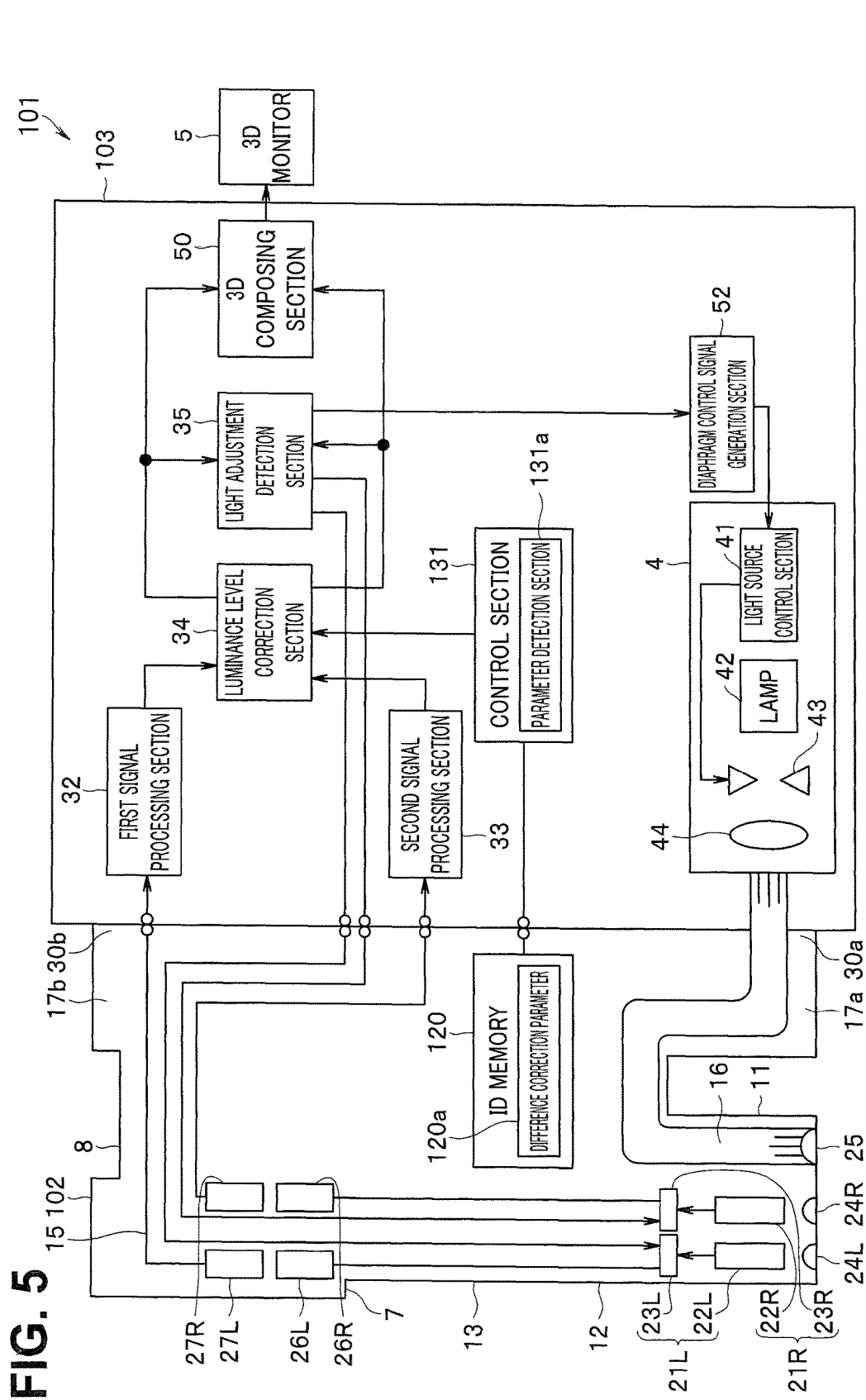
FIG. 5 is a block diagram illustrating a configuration of an endoscope system according to a second embodiment of the present invention.

FIG. 5 is a diagram illustrating a configuration of the endoscope system according to the second embodiment of the present invention. As illustrated in FIG. 5, an endoscope system 101 according to the second embodiment has a basic configuration similar to the configuration of the first embodiment; however, is different from the first embodiment in that an ID memory 120 provided in a stereoscopic endoscope 102 holds "difference information" of sensitivity characteristics of the two right and left image pickup devices mounted on the stereoscopic endoscope 102, as mentioned above. Therefore, description is given of a part different from the first embodiment, and description of a part similar to the first embodiment is omitted.

As illustrated in FIG. 5, the signal connector 30*b* of the stereoscopic endoscope 102 is provided with the ID memory 120 that serves as a memory section holding information of each stereoscopic endoscope 102. The ID memory 120 holds a difference correction parameter 120*a* that is the "difference information" of the sensitivity characteristics between the image pickup device 23L for the left image and the image pickup device 23R for the right image that are mounted on the stereoscopic endoscope 102, in the second embodiment.

The difference correction parameter 120*a* is a correction parameter to correct the luminance level of the image expressed by one of the first image pickup signal relating to the image pickup device 23L for the left image and the second image pickup signal relating to the image pickup device 23R for the right image, to be equivalent to the luminance level of the image expressed by the other image pickup signal.

Moreover, a control section 131 in a processor 103 controls various kinds of circuits in the processor 103, and includes a parameter detection section 131*a*. The parameter detection section 131*a* detects the difference correction parameter 120*a* that is the "difference information" held by the ID memory 120 of the stereoscopic endoscope 102.

The luminance level correction section 34 in the second embodiment performs, under the control of the control section 131, the predetermined correction processing on one of the right and left image pickup signals to correct the difference of the sensitivity characteristics between the two right and left solid-state image pickup devices, based on the difference correction parameter 120*a* detected by the parameter detection section 131*a*.

<Action of Second Embodiment>

Next, action of the processor in the endoscope system according to the second embodiment is described.

When the stereoscopic endoscope 102 is connected to the processor 103, the control section 131 detects, through the parameter detection section 131*a*, the difference correction parameter 120*a* held by the ID memory 120.

Thereafter, the luminance level correction section 34 performs, under the control of the control section 131, the correction processing on the second image pickup signal as the output signal of the second signal processing section 33 such that the luminance level of the second image pickup signal becomes equal to the luminance level of the first image pickup signal as the output signal of the first signal processing section 32, based on the difference correction parameter 120*a* detected by the parameter detection section 131*a*.

Then, the luminance level correction section 34 outputs, as the second corrected image pickup signal, the second image pickup signal subjected to the correction processing, while outputting the first image pickup signal as is that is the output signal of the first signal processing section 32.

Note that the difference correction parameter 120*a* is the parameter relating to the difference of the sensitivity of the image pickup device 23R for the right image with respect to the sensitivity of the image pickup device 23L for the left image in the present embodiment; however, the difference correction parameter 120*a* is not limited to the above-described parameter. The difference correction parameter 120*a* may be a parameter relating to the difference of the sensitivity of the image pickup device 23L for the left image with respect to the sensitivity of the image pickup device 23R for the right image.

In this case, the luminance level correction section 34 performs, under the control of the control section 131, the correction processing on the first image pickup signal as the output signal of the first signal processing section 32 such that the luminance level of the first image pickup signal becomes equal to the luminance level of the second image pickup signal as the output signal of the second signal processing section 33, based on the difference correction parameter 120*a* detected by the parameter detection section 131*a*.

The description of action of the subsequent light adjustment detection section 35 and the subsequent 3D composing section 50 is omitted because the action is similar to the action of the first embodiment.

As described above, even if the difference of the sensitivity characteristics occurs between the two solid-state image pickup devices to be mounted on the endoscope due to variation or other causes, the endoscope system according to the second embodiment corrects the difference of the sensitivity characteristics between the two right and left solid-state image pickup devices on the processor 3 side, as with the first embodiment. Therefore, it is not necessary to provide the light adjustment detection section 35 for each of the two image pickup signals, and only one light adjustment detection section 35 is sufficient, which results in reduction of the cost.

Note that, in the first and second embodiments, attention is paid on the difference of the sensitivity characteristics between the two solid-state image pickup devices to be mounted on the endoscope. The present invention, however, may be adopted to, for example, not only a case in which difference occurs in the sensitivity characteristics caused by the solid-state image pickup device itself but also a case in which difference occurs in sensitivity characteristics caused by component processing accuracy, assembling accuracy, or the like of the image pickup optical system, without limitation.

In other words, the ID memory holds the correction parameter relating to the sensitivity characteristics of the entire image pickup optical system including the solid-state image pickup devices, which makes it possible to correct the difference of the sensitivity characteristics even if the difference of the sensitivity characteristics occurs between two image pickup optical systems. Therefore, it is possible to reduce the cost only by providing one light adjustment detection section as with the above-described embodiments.

In addition, in the first and second embodiments, the technology is described in which attention is paid on the difference of the sensitivity characteristics (the difference of the luminance level) between the two solid-state image pickup devices to be mounted on the endoscope, and the parameters used to correct the difference of the characteristics are held and used. The present invention is also applicable to a technology of correcting difference of the other characteristics.

For example, the present invention is applicable to a gradation correction technology of correcting difference of gradation characteristics for each pixel between two solid-state image pickup devices, a color tone correction technology of correcting difference of color tone characteristics for each pixel between two solid-state image pickup devices, an eccentricity correction technology of correcting parallax of a stereoscopic image to a predetermined parallax, a white spot correction technology of correcting white spot pixels in two solid-state image pickup devices, and other technologies.

Embodiments in which the present invention is applied to the correction technologies are described below.

(Third Embodiment)

Next, a third embodiment of the present invention is described.

The third embodiment is an embodiment in which the present invention is applied to the gradation correction technology of correcting the difference of the gradation characteristics for each pixel between the two solid-state image pickup devices. In other words, in the present embodiment, a left correction parameter 220*a* and a right correction parameter 220*b* are information used to correct the difference of the gradation characteristics for each pixel between the two right and left solid-state image pickup devices on the stereoscopic endoscope side.

Figure 6:
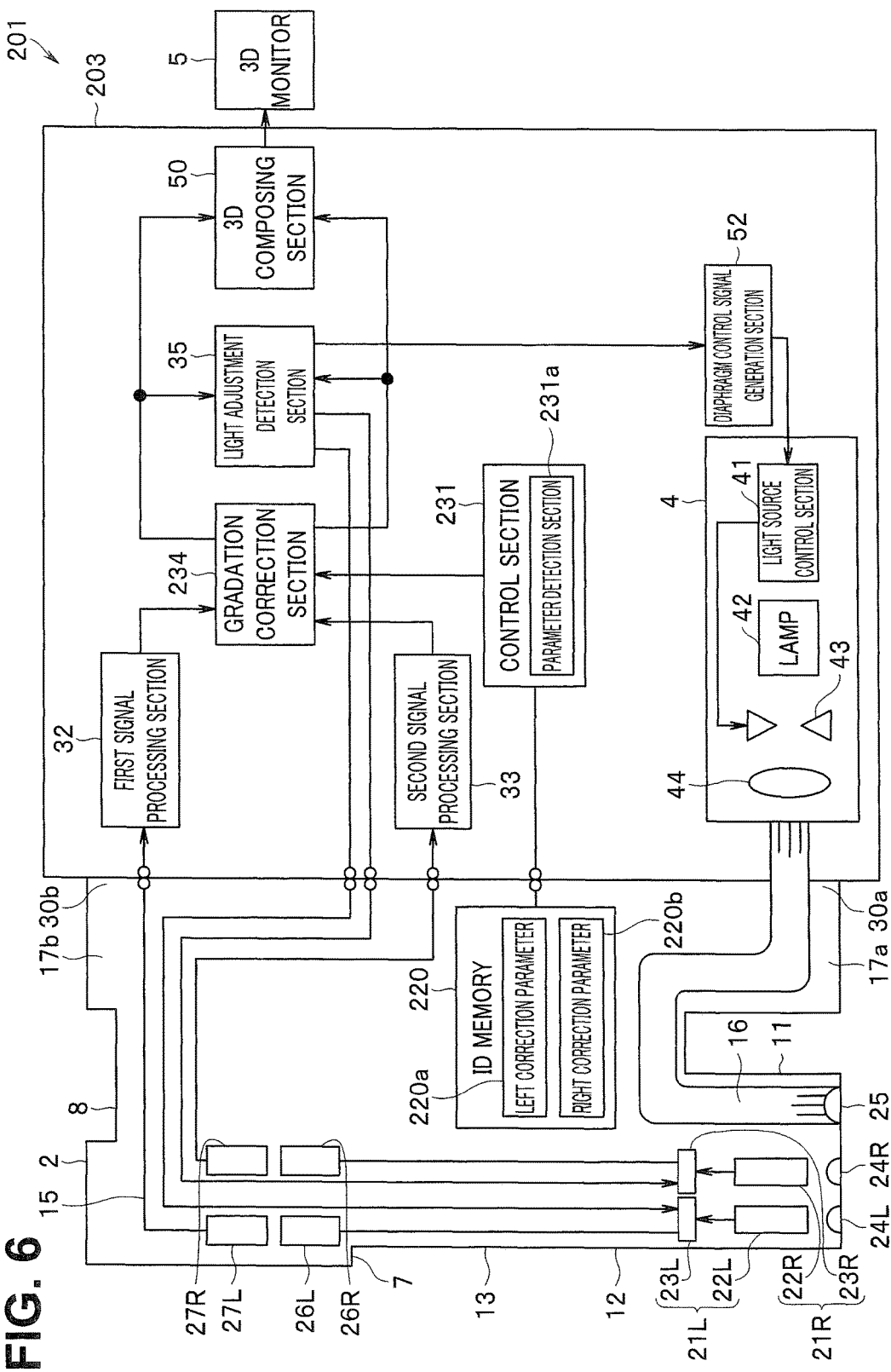
FIG. 6 is a block diagram illustrating a configuration of an endoscope system according to a third embodiment of the present invention.

FIG. 6 is a diagram illustrating a configuration of an endoscope system 201 according to the third embodiment.

As illustrated in FIG. 6, a processor 203 according to the present embodiment includes a control section 231, in addition to the unillustrated power supply circuit, the unillustrated CCD drive circuit, the first signal processing section 32, the second signal processing section 33, the light adjustment detection section 35, and the 3D composing section 50 that are similar to the circuits and the sections of the first embodiment. The power supply circuit generates the plurality of power supply voltages necessary for operation of the image pickup devices and other devices. The control section 231 controls various kinds of circuits in the processor 203.

The control section 231 controls the various kinds of circuits in the processor 203 as mentioned above, and includes a parameter detection section 231*a*. The parameter detection section 231*a* detects gradation parameter information held by the ID memory 220 in the signal connector 30*b* of the stereoscopic endoscope 2.

The processor 203 also includes a gradation correction section 234. The gradation correction section 234 is connected to the respective output ends of the first signal processing section 32 and the second signal processing section 33, and performs, under the control of the control section 231, gradation correction processing on the image pickup signals that have been respectively subjected to the predetermined processing by the first signal processing section 32 and the second signal processing section 33.

The gradation correction section 234 performs, under the control of the control section 231, the correction processing on the first image pickup signal and the second image pickup signal that are the respective output signals of the first signal processing section 32 and the second signal processing section 33, such that the first image pickup signal and the second image pickup signal have respective predetermined gradation, based on the left correction parameter 220a and the right correction parameter 220b that are detected by the parameter detection section 231a in the control section 231. The gradation correction section 234 then outputs the processed image pickup signals to the following stage.

<Correction Parameter in Third Embodiment>

In the endoscope system 201 according to the third embodiment, the left correction parameter 220a is a first correction parameter that causes the gradation correction section 234 to correct the first image pickup signal such that the gradation of the image expressed by the first image pickup signal relating to the image pickup device 23L for the left image becomes a predetermined value, according to the gradation characteristics derived from physical characteristics of the image pickup device 23L for the left image itself.

On the other hand, the right correction parameter 220b is a second correction parameter that causes the gradation correction section 234 to correct the second image pickup signal such that the gradation of the image expressed by the second image pickup signal relating to the image pickup device 23R for the right image becomes a predetermined value, according to the gradation characteristics derived from physical characteristics of the image pickup device 23R for the right image itself.

Further, in the present embodiment, the gradation correction section 234 performs the correction processing such that the gradation of the image expressed by the first image pickup signal becomes equal to the gradation of the image expressed by the second image pickup signal, based on the left correction parameter 220a and the right correction parameter 220b.

The description of other components and action is omitted because the other components and the action are similar to the components and the action of the first embodiment.

As described above, according to the third embodiment, even if the difference of the gradation characteristics occurs between the two solid-state image pickup devices to be mounted on the endoscope due to variation or other causes, it is possible to correct the difference of the gradation characteristics between the two right and left solid-state image pickup devices on the processor side.

(Fourth Embodiment)

Next, a fourth embodiment of the present invention is described.

The fourth embodiment is an embodiment in which the present invention is applied to the color tone correction technology of correcting the difference of color tone characteristics for each pixel between the two solid-state image pickup devices. In other words, in the present embodiment, a left correction parameter 320a and a right correction parameter 320b are information used to correct the difference of the color tone characteristics for each pixel between the two right and left solid-state image pickup devices on the stereoscopic endoscope side.

Figure 7:
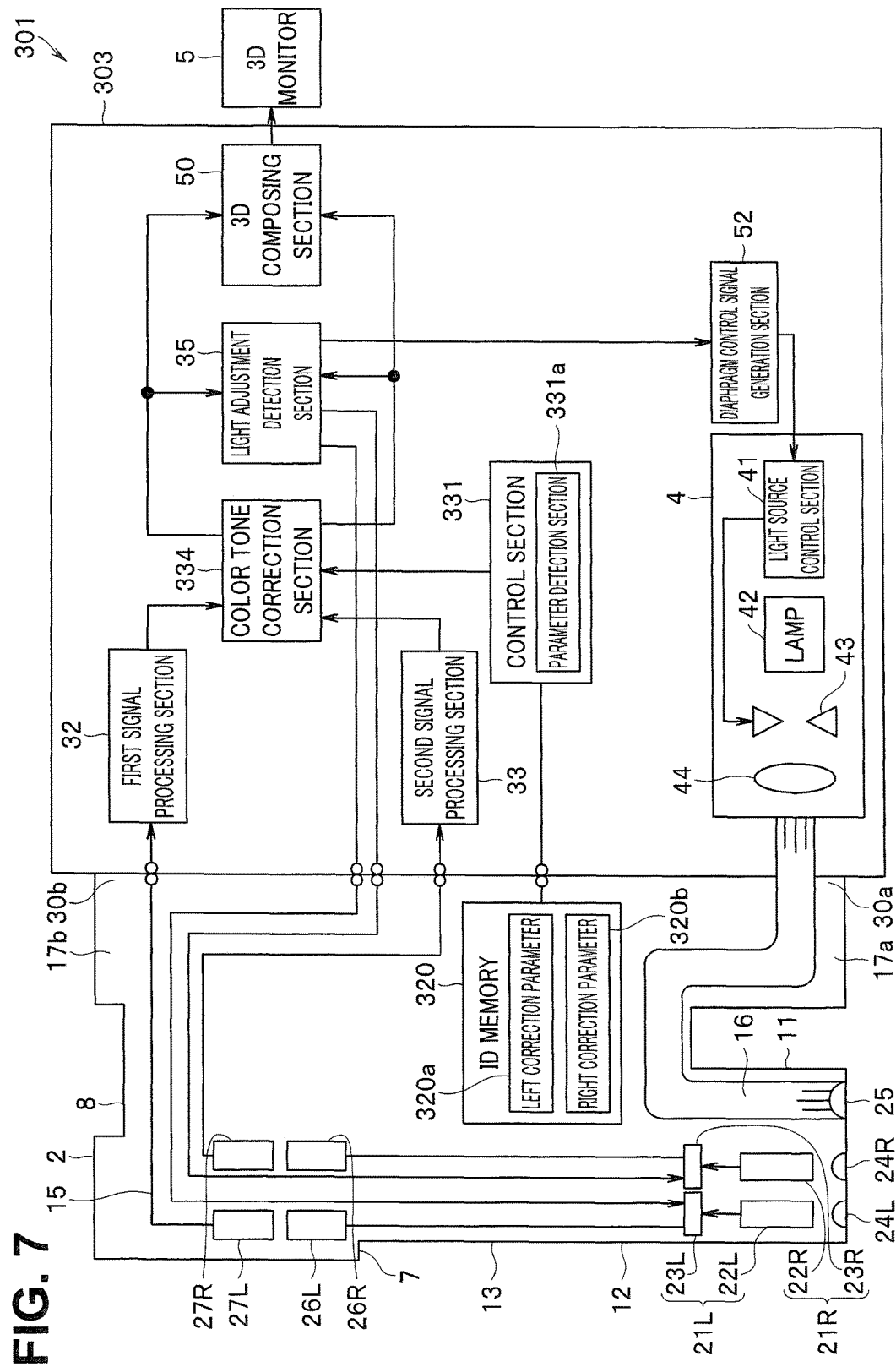
FIG. 7 is a block diagram illustrating a configuration of an endoscope system according to a fourth embodiment of the present invention.

FIG. 7 is a diagram illustrating a configuration of an endoscope system 301 according to the fourth embodiment.

As illustrated in FIG. 7, a processor 303 according to the present embodiment includes a control section 331, in addition to the unillustrated power supply circuit, the unillustrated CCD drive circuit, the first signal processing section 32, the second signal processing section 33, the light adjustment detection section 35, and the 3D composing section 50 that are similar to the circuits and the sections of the first embodiment. The power supply circuit generates the plurality of power supply voltages necessary for operation of the image pickup devices and other devices. The control section 331 controls various kinds of circuits in the processor 303.

The control section 331 controls the various kinds of circuits in the processor 303 as mentioned above, and includes a parameter detection section 331a. The parameter detection section 331a detects color tone parameter information held by an ID memory 320 in the signal connector 30b of the stereoscopic endoscope 2.

The processor 303 also includes a color tone correction section 334. The color tone correction section 334 is connected to the respective output ends of the first signal processing section 32 and the second signal processing section 33, and performs, under the control of the control section 331, color tone correction processing on the image pickup signals that have been respectively subjected to the predetermined processing by the first signal processing section 32 and the second signal processing section 33.

The color tone correction section 334 performs, under the control of the control section 331, the correction processing on the first image pickup signal and the second image pickup signal that are the respective output signals of the first signal processing section 32 and the second signal processing section 33, such that the first image pickup signal and the second image pickup signal have respective predetermined color tone, based on the left correction parameter 320a and the right correction parameter 320b that are detected by the parameter detection section 331a in the control section 331. The color tone correction section 334 then outputs the processed image pickup signals to the following stage.

<Correction Parameter in Fourth Embodiment>

In the endoscope system 301 according to the fourth embodiment, the left correction parameter 320a is a first correction parameter that causes the color tone correction section 334 to correct the first image pickup signal such that the color tone of the image expressed by the first image pickup signal relating to the image pickup device 23L for the left image becomes a predetermined value, according to the color tone characteristics derived from physical characteristics of the image pickup device 23L for the left image itself.

On the other hand, the right correction parameter 320b is a second correction parameter that causes the color tone correction section 334 to correct the second image pickup signal such that the color tone of the image expressed by the second image pickup signal relating to the image pickup device 23R for the right image becomes a predetermined value, according to the color tone characteristics derived from physical characteristics of the image pickup device 23R for the right image itself.

Further, in the present embodiment, the color tone correction section 334 performs the correction processing such that the color tone of the image expressed by the first image pickup signal becomes equal to the color tone of the image expressed by the second image pickup signal, based on the left correction parameter 320a and the right correction parameter 320b.

The description of other components and action is omitted because the other components and the action are similar to the components and the action of the first embodiment.

As described above, according to the fourth embodiment, even if the difference of the color tone characteristics occurs between the two solid-state image pickup devices to be mounted on the endoscope due to variation or other causes, it is possible to correct the difference of the color tone characteristics between the two right and left solid-state image pickup devices on the processor side.

(Fifth Embodiment)

Next, a fifth embodiment of the present invention is described.

The fifth embodiment is an embodiment in which the present invention is applied to the eccentricity correction technology of performing correction such that parallax of a stereoscopic image becomes a predetermined parallax. In other words, in the present embodiment, a left correction parameter 420a and a right correction parameter 420b are information used to perform correction such that parallax of a stereoscopic image that is an output image of the 3D composing section becomes the predetermined parallax.

Figure 8:
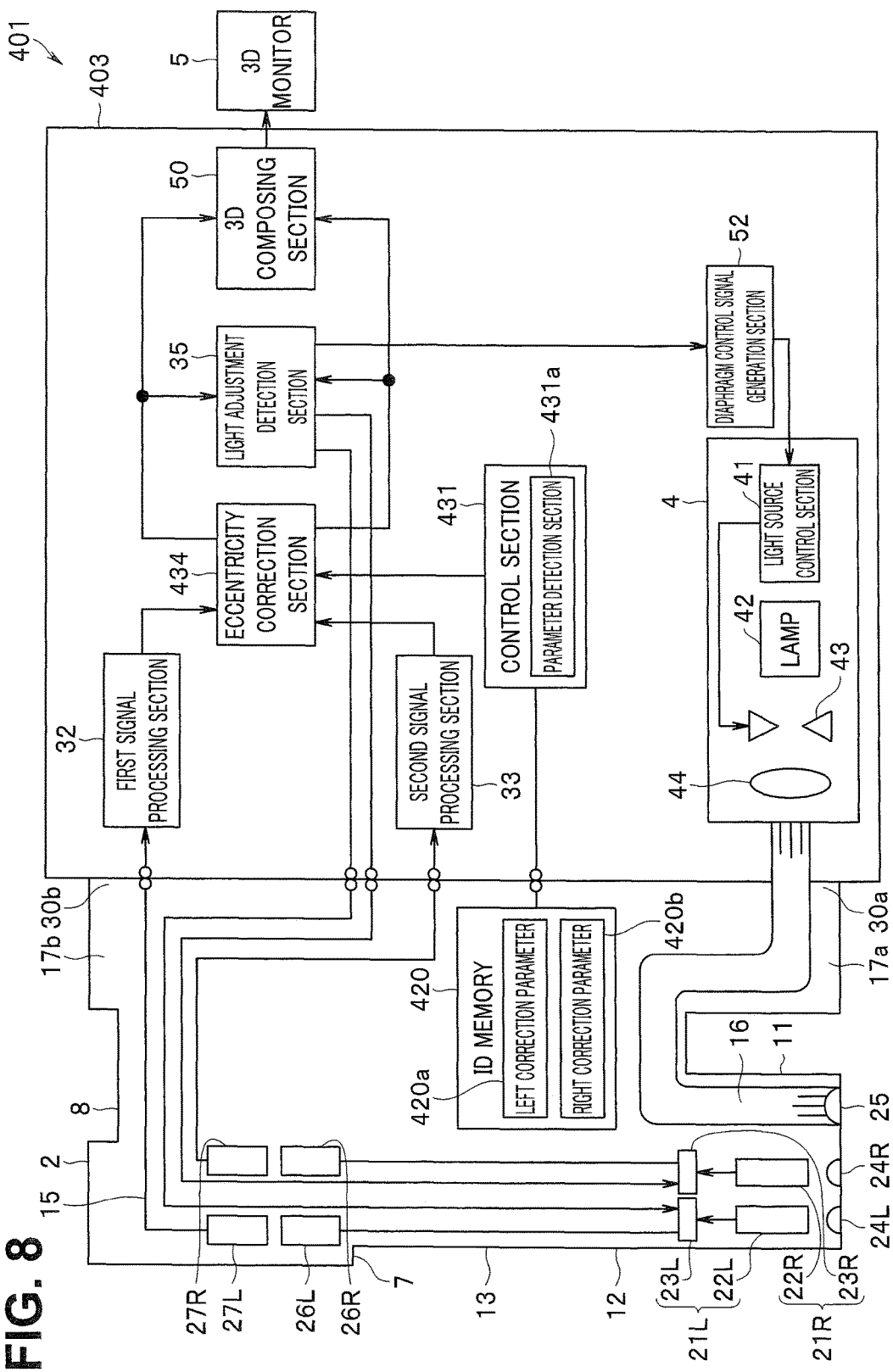
FIG. 8 is a block diagram illustrating a configuration of an endoscope system according to a fifth embodiment of the present invention.

FIG. 8 is a diagram illustrating a configuration of an endoscope system 401 according to the fifth embodiment.

As illustrated in FIG. 8, a processor 403 according to the present embodiment includes a control section 431, in addition to the unillustrated power supply circuit, the unillustrated CCD drive circuit, the first signal processing section 32, the second signal processing section 33, the light adjustment detection section 35, and the 3D composing section 50 that are similar to the circuits and the sections of the first embodiment. The power supply circuit generates the plurality of power supply voltages necessary for operation of the image pickup devices and other devices. The control section 431 controls various kinds of circuits in the processor 403.

The control section 431 controls the various kinds of circuits in the processor 403 as mentioned above, and includes a parameter detection section 431a. The parameter detection section 431a detects eccentricity parameter information held by an ID memory 420 in the signal connector 30b of the stereoscopic endoscope 2.

The processor 403 also includes an eccentricity correction section 434. The eccentricity correction section 434 is connected to the respective output ends of the first signal processing section 32 and the second signal processing section 33, and performs, under the control of the control section 431, eccentricity correction processing on the image pickup signals that have been respectively subjected to the predetermined processing by the first signal processing section 32 and the second signal processing section 33.

The eccentricity correction section 434 performs, under the control of the control section 431, the correction processing on the first image pickup signal and the second image pickup signal that are the respective output signals of the first signal processing section 32 and the second signal processing section 33, such that parallax of a stereoscopic image as the output image of the 3D composing section 50 becomes the predetermined parallax, based on the left correction parameter 420a and the right correction parameter 420b that are detected by the parameter detection section 431a in the control section 431. The eccentricity correction section 434 then outputs the processed image pickup signals to the following stage.

<Correction Parameter in Fifth Embodiment>

In the endoscope system 401 according to the fifth embodiment, the left correction parameter 420a is a first correction parameter that causes the eccentricity correction section 434 to correct the first image pickup signal such that the parallax of the image expressed by the first image pickup signal relating to the image pickup device 23L for the left image becomes a predetermined value.

On the other hand, the right correction parameter 420b is the second correction parameter that causes the eccentricity correction section 434 to correct the second image pickup signal such that the parallax of the image expressed by the second image pickup signal relating to the image pickup device 23R for the right image becomes a predetermined value.

Further, in the present embodiment, the eccentricity correction section 434 performs the correction processing such that the parallax of the stereoscopic image as the output image of the 3D composing section becomes the predetermined parallax, based on the left correction parameter 420a and the right correction parameter 420b.

The description of other components and action is omitted because the other components and the action are similar to the components and the action of the first embodiment.

As described above, according to the fifth embodiment, even if the parallax of the stereoscopic image as the output image of the 3D composing section does not become a proper value due to variation of the two solid-state image pickup devices to be mounted on the endoscope, component processing accuracy or assembling accuracy of the image pickup optical system, other causes, it is possible to correct the parallax of the two right and left solid-state image pickup devices on the processor side, which allows for proper display of the stereoscopic image as the output image of the 3D composing section.

(Sixth Embodiment)

Next, a sixth embodiment of the present invention is described.

The sixth embodiment is an embodiment in which the present invention is applied to the white spot correction technology of correcting the white spot pixels of the two solid-state image pickup devices and other technologies. In other words, in the present embodiment, a left correction parameter 520a and a right correction parameter 520b are information used to correct the white spot pixels of the two solid-state image pickup devices.

Figure 9:
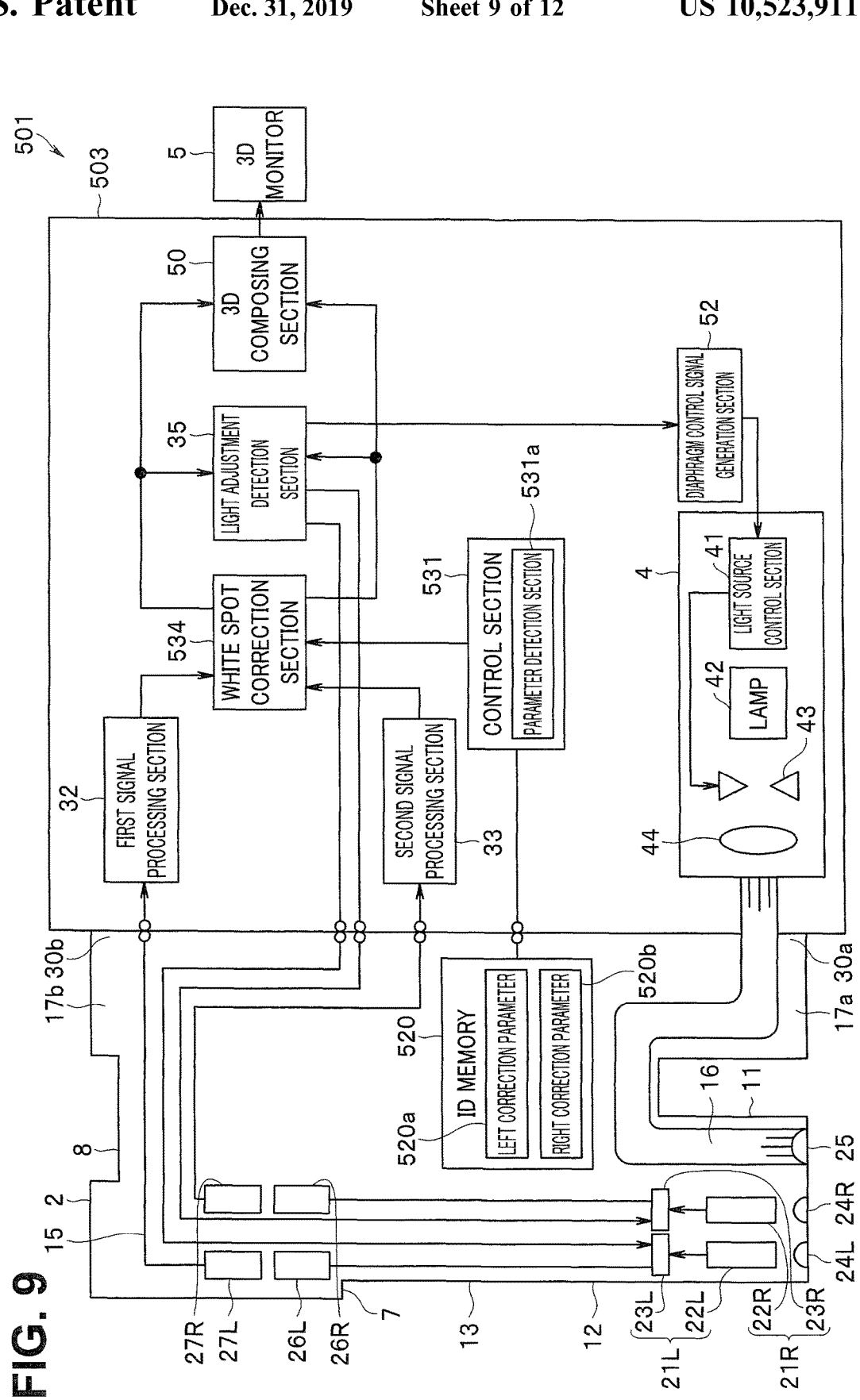
FIG. 9 is a block diagram illustrating a configuration of an endoscope system according to a sixth embodiment of the present invention.

FIG. 9 is a diagram illustrating a configuration of an endoscope system 501 according to the sixth embodiment.

As illustrated in FIG. 9, a processor 503 according to the present embodiment includes a control section 531, in addition to the unillustrated power supply circuit, the unillustrated CCD drive circuit, the first signal processing section 32, the second signal processing section 33, the light adjustment detection section 35, and the 3D composing section 50 that are similar to the circuits and the sections of the first embodiment. The power supply circuit generates the plurality of power supply voltages necessary for operation of the image pickup devices and other devices. The control section 531 controls various kinds of circuits in the processor 503.

The control section 531 controls the various kinds of circuits in the processor 503 as mentioned above, and includes a parameter detection section 531a. The parameter detection section 531a detects color tone parameter information held by an ID memory 520 in the signal connector 30b of the stereoscopic endoscope 2.

The processor 503 also includes a white spot correction section 534. The white spot correction section 534 is connected to the respective output ends of the first signal processing section 32 and the second signal processing section 33, and performs, under the control of the control section 531, white spot correction processing on the image pickup signals that have been respectively subjected to the predetermined processing by the first signal processing section 32 and the second signal processing section 33.

The white spot correction section 534 performs, under the control of the control section 531, the correction processing to correct the whit spot pixel of the first image pickup signal and the second image pickup signal that are the respective output signals of the first signal processing section 32 and the second signal processing section 33, based on the left correction parameter 520a and the right correction parameter 520b that are detected by the parameter detection section 531a in the control section 531. The white spot correction section 534 then outputs the processed image pickup signals to the following stage.

<Correction Parameter in Sixth Embodiment>

In the endoscope system 501 according to the sixth embodiment, the left correction parameter 520a is a first correction parameter relating to coordinate position information of the white spot pixel in the first image pickup signal.

On the other hand, the right correction parameter 520b is a second correction parameter relating to coordinate position information of the white spot pixel in the second image pickup signal.

Further, in the present embodiment, the white spot correction section 534 performs the correction processing on the white spot pixels through a predetermined correction method, based on the left correction parameter 520a and the right correction parameter 520b.

The description of other components and action is omitted because the other components and the action are similar to the components and the action of the first embodiment.

As described above, according to the sixth embodiment, even if white spots occur in the two solid-state image pickup devices to be mounted on the endoscope, it is possible to appropriately perform the correction on the processor side, based on the coordinate position information of the white spots.

Note that, in the respective processors according to the first to sixth embodiments, the correction processing sections such as the luminance level correction section 34 are disposed in the rear stage of the first signal processing section 32 and the second signal processing section 33, and further, the light adjustment detection section 35 is disposed in the rear stage of the correction processing section.

The invention of the present application, however, is not limited to the layout, and is applicable to an endoscope system in which a light adjustment detection section that exerts action and effects equivalent to the action and the effects of the light adjustment detection section 35 is disposed in the front stage of the first signal processing section 32 and the second signal processing section 33, and the light adjustment detection processing is performed on the image pickup signals prior to the correction processing by the correction processing section.

(Seventh Embodiment)

Next, a seventh embodiment of the present invention is described.

Incidentally, in recent years, 3D observation has been highly demanded in an operation observation apparatus. In addition, in the 3D observation, a technology of performing the 3D observation using an eyewear dedicated for the 3D observation is well-known; however, a visual field is darkened in the technology using the dedicated eyewear. Therefore, a technology in which brightness is adjusted only when a 3D signal is detected on the monitor side is also known.

However, since only the 3D signal is detected in the technology, only constant adjustment is performed irrespective of the brightness of image data. Therefore, an image actually observed with use of the eyewear dedicated for the 3D observation is disadvantageously darkened as compared with the 2D observation.

Figure 10:
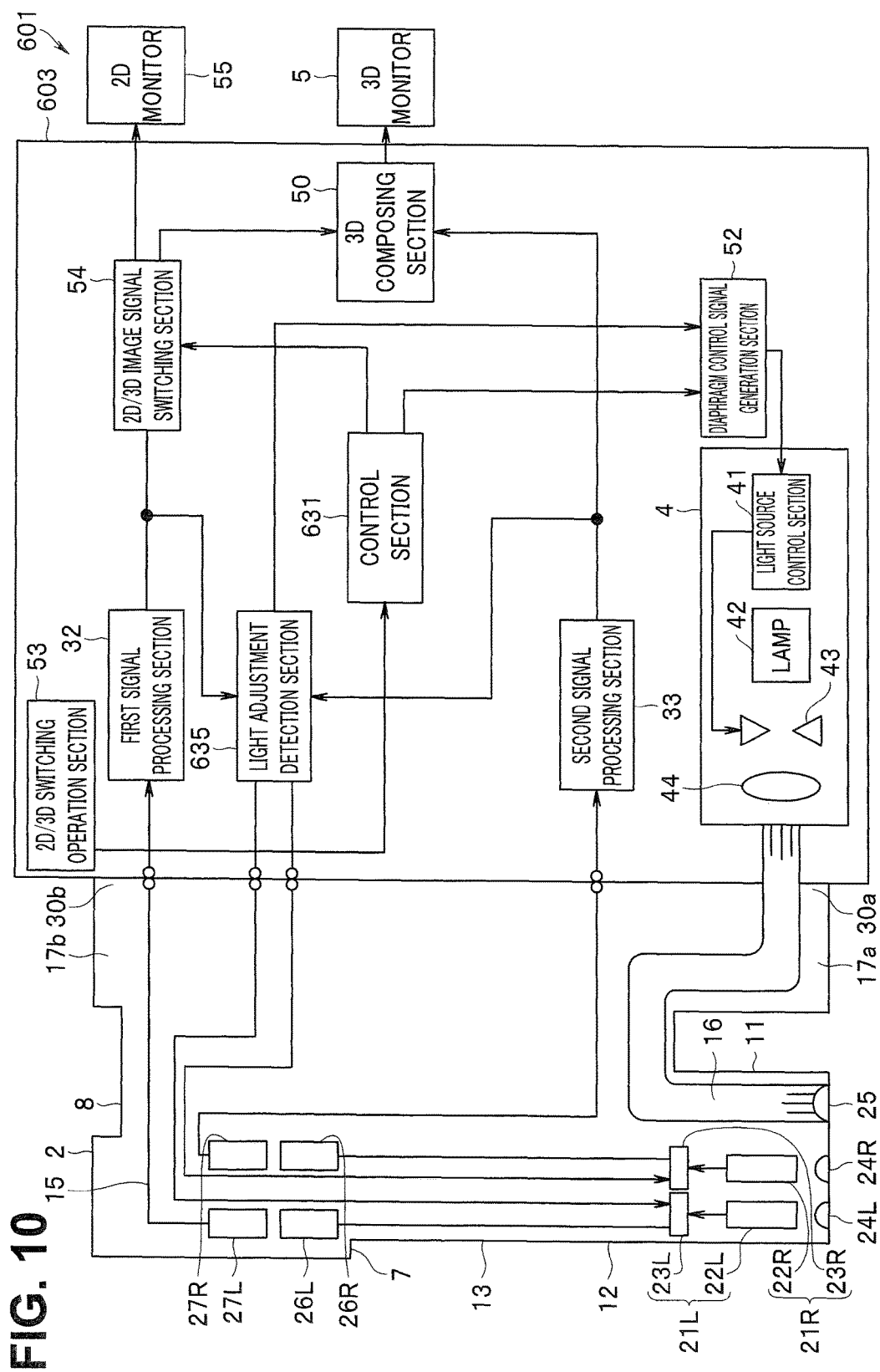
FIG. 10 is a block diagram illustrating a configuration of an endoscope system according to a seventh embodiment of the present invention.

The seventh embodiment is made for such a disadvantage, and FIG. 10 is a diagram illustrating an endoscope system according to the seventh embodiment.

An endoscope system 601 according to the seventh embodiment is an endoscope system that picks up an image with use of the stereoscopic endoscope 2 as with the first and second embodiments. The endoscope system 601 includes a switching mechanism of 2D and 3D and reproduces 2D image on the 2D monitor, in addition to display of the 3D image on the 3D monitor.

Next, a processor 603 in the endoscope system 601 according to the seventh embodiment is described.

As illustrated in FIG. 10, the processor 603 according to the present embodiment includes a control section 631, the first signal processing section 32, and the second signal processing section 33. The control section 631 controls various kinds of circuits in the processor 603. The first signal processing section 32 receives the first image pickup signal out of the two image pickup signals in the stereoscopic endoscope 2 and performs the predetermined signal processing on the first image pickup signal under the control of the control section 631. The first image pickup signal has been generated by the image pickup device 23L for the left image, and has passed through the CDS circuit 26L and the A/D conversion circuit 27L, as mentioned above. The second signal processing section 33 receives the second image pickup signal and performs the predetermined signal processing on the second image pickup signal under the control of the control section 631. The second image pickup signal has been generated by the image pickup device 23R for the right image and has passed through the CDS circuit 26R and the A/D conversion circuit 27R.

The control section 631 includes a threshold comparing section that compares the luminance value of one of the first image pickup signal and the second image pickup signal that have been respectively processed by the first signal processing section 32 and the second signal processing section 33, with a predetermined threshold.

The first signal processing section 32 and the second signal processing section 33 respectively perform the predetermined signal processing on the image pickup signals from the image pickup device 23L and the image pickup device 23R. The first signal processing section 32 and the second signal processing section 33 each include well-known signal processing sections such as an automatic gain control circuit (AGC circuit), a white balance circuit, a gamma correction circuit, a magnification reduction circuit, and a contour enhancement circuit, thereby respectively performing the signal processing in a manner similar to the above.

In addition, the processor 603 includes a light adjustment detection section 635 and the 3D composing section 50. The light adjustment detection section 635 performs light adjustment detection of the first image pickup signal processed by the first signal processing section 32 or the second image pickup signal processed by the second signal processing section 33. The 3D composing section 50 composes the first image pickup signal processed by the first signal processing section 32 and the second image pickup signal processed by the second signal processing section 33 to generate a predetermined 3D image signal.

The processor 603 further includes a 2D/3D switching operation section 53 and a 2D/3D image signal switching section 54. The 2D/3D switching operation section 53 performs switching operation of 2D and 3D. The 2D/3D image signal switching section 54 is connected to the output part of the first signal processing section 32.

The 2D/3D image signal switching section 54 includes an output end connectable to the 2D monitor 55 on the outside of the processor 603, and an output end connectable to the 3D composing section 50. The 2D/3D image signal switching section 54 switches, under the control of the control section 631, whether the first image pickup signal outputted from the first signal processing section 32 is used as the 2D signal or used as the 3D composing signal together with the second image pickup signal, according to the operation of the 2D/3D switching operation section 53.

The light adjustment detection section 635 performs a well-known light adjustment detection function as with the above description. The light adjustment detection section 635 includes a photometry section that measures luminance of the first corrected image pickup signal and luminance of the second corrected image pickup signal, and outputs information signals relating to the respective measured luminance values.

Moreover, the light adjustment detection section 635 includes an exposure time control section that controls an exposure time of the image pickup device 23L for the left image and the image pickup device 23R for the right image, according to the luminance values measured by the photometry section, as with the above description. The exposure time control section generates, according to the measured luminance values, control signals for electronic shutter control of the image pickup device 23L for the left image and the image pickup device 23R for the right image, thereby transmitting the control signals to the image pickup device 23L for the left image and the image pickup device 23R for the right image.

Note that, in the seventh embodiment, the light adjustment detection section 635 controls, under the control of the control section 631, an information signal relating to the luminance values provided from the photometry section, according to the switching operation of 2D and 3D by the 2D/3D switching operation section 53.

Further, in the seventh embodiment, the light adjustment detection section 635 controls, under the control of the control section 631, the control signals provided from the exposure time control section, according to the switching operation of 2D and 3D by the 2D/3D switching operation section 53.

The processor 603 further includes the diaphragm control signal generation section 52 that generates the diaphragm control signal to control the diaphragm in the light source section 4, according to the information signal relating to the measured luminance values provided from the light adjustment detection section 635.

In addition, in the present embodiment, the processor 603 includes therein the light source section 4 as with the above description. The light source section 4 emits illumination light to the light guide cable 16 in order to supply the illumination light to the stereoscopic endoscope 2.

The light source section 4 includes the lamp 42, the diaphragm 43, the lens 44, and the light source control section 41. Illumination light from the lamp 42 is outputted toward the lens 44 through the diaphragm 43 that is controlled by the light source control section 41. In addition, the lens 44 condenses light on the proximal end portion of the light guide cable 16.

Further, the light condensed on the proximal end portion of the light guide cable 16 is outputted from the distal end portion of the light guide cable 16 after being transmitted through the light guide cable 16, as illumination light to be supplied to the stereoscopic endoscope 2.

The light source control section 41 controls the diaphragm 43, based on the diaphragm control signal generated by the diaphragm control signal generation section 52.

<Action of Seventh Embodiment>

Next, action of the endoscope system according to the seventh embodiment is described.

The control section 631 confirms the operation state of the 2D/3D switching operation section 53. When a mode of outputting the 2D image signal is selected, the control section 631 controls and switches the 2D/3D image signal switching section 54 to use the first image pickup signal outputted from the first signal processing section 32 as the 2D signal.

Further, when the mode of outputting the 2D image signal (hereinafter, referred to as a 2D outputting mode) is selected, the control section 631 controls the light adjustment detection section 635 to control, as the signal for the 2D outputting mode, the information signal relating to the luminance values provided from the photometry section of the light adjustment detection section 635 and to control, as the signal for the 2D outputting mode, the control signals provided from the exposure time control section.

On the other hand, when a mode of outputting the 3D image signal (hereinafter, referred to as a 3D outputting mode) is selected in the confirmation of the operation state of the 2D/3D switching operation section 53, the control section 631 controls and switches the 2D/3D image signal switching section 54 to use the first image pickup signal outputted from the first signal processing section 32 as the 3D composing signal.

Further, when the mode of outputting the 3D image signal is selected, the control section 631 controls the light adjustment detection section 635 to control, as the signal for the 3D outputting mode, the information signal relating to the luminance values provided from the photometry section of the light adjustment detection section 635 and to control, as the signal for the 3D outputting mode, the control signals provided from the exposure time control section.

More specifically, when the 3D outputting mode is selected, the control section 631 performs control such that brightness (the luminance value) of an object image to be picked up becomes larger by a predetermined value than the brightness when the 2D outputting mode is selected.

The predetermined value relating to the luminance value is a value sufficient to secure brightness similar to the brightness in the 2D observation even if the dedicated 3D eyewear is worn in the 3D observation.

As described above, when the 3D outputting mode is selected, the endoscope system according to the seventh embodiment automatically performs control such that the brightness (the luminance value) of the object image to be picked up becomes larger by the predetermined value than the brightness when the 2D outputting mode is selected. This makes it possible to secure brightness similar to the brightness in the 2D observation even if the dedicated 3D eyewear is worn in the 3D observation.

(Eighth Embodiment)

Next, an eighth embodiment of the present invention is described with reference to FIG. 11.

Figure 11:
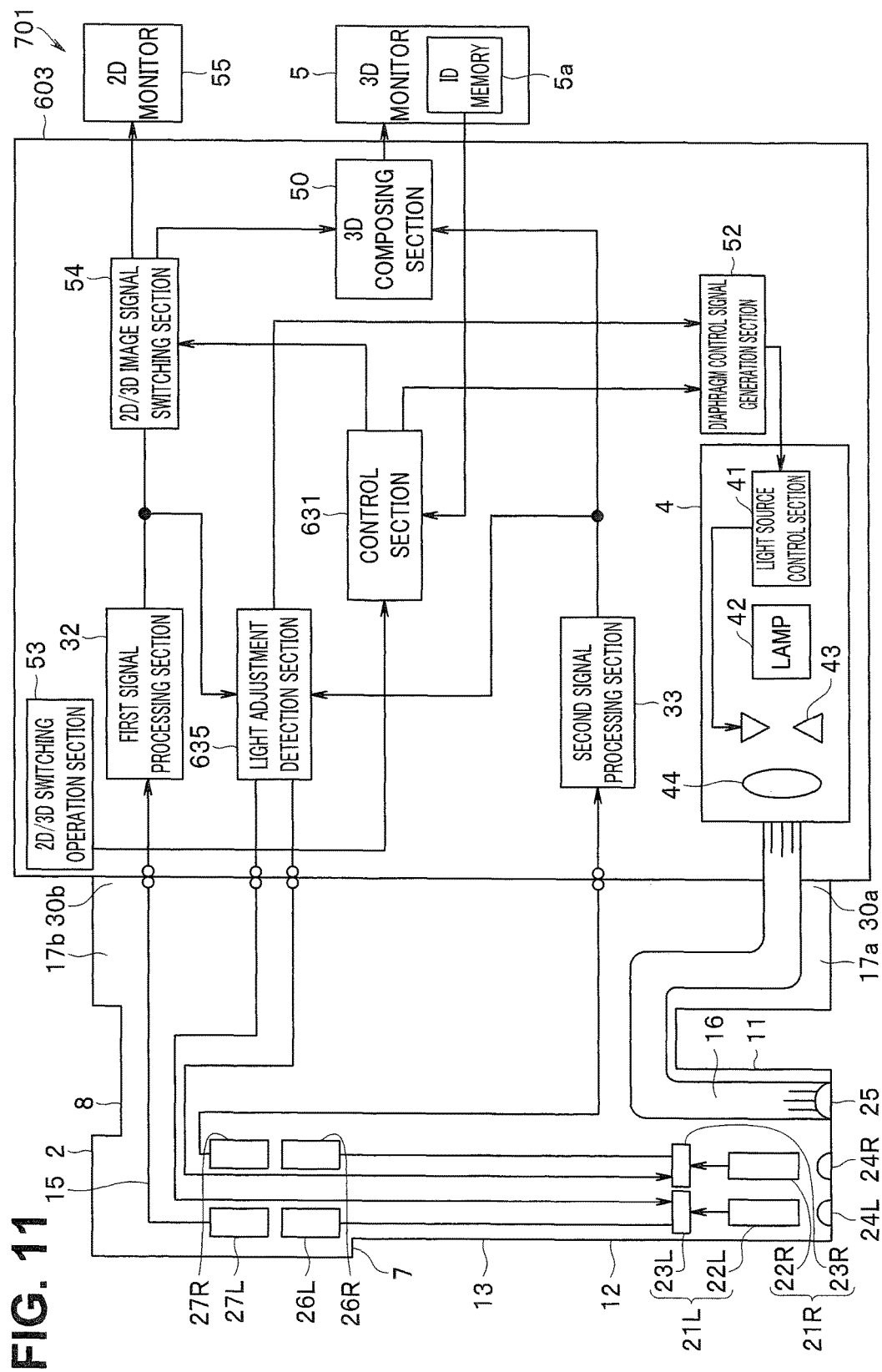
FIG. 11 is a block diagram illustrating a configuration of an endoscope system according to an eighth embodiment of the present invention.

As illustrated in FIG. 11, an endoscope system 701 according to the eighth embodiment is an endoscope system that has a basic configuration similar to the endoscope system 601 of the seventh embodiment, and picks up an image with use of the stereoscopic endoscope 2 as with the first and second embodiments. The endoscope system 701 includes a switching mechanism of 2D and 3D and reproduces a 2D image on the 2D monitor in addition to display of a 3D image on the 3D monitor.

Further, in the eighth embodiment, brightness of the object image to be picked up is adjusted according to the characteristics of the 3D monitor itself. The other components and action are similar to the components and the action of the seventh embodiment. Therefore, only difference with the seventh embodiment is described, and the detailed description of the components and the action similar to the components and the action of the seventh embodiment is omitted.

As illustrated in FIG. 11, the processor 603 according to the eighth embodiment has a configuration similar to the configuration of the processor according to the seventh embodiment; however, the control section 631 acquires information of an ID memory 5a that is installed in the 3D monitor 5 connected to the processor 603.

In this case, when the 3D outputting mode is selected by the 2D/3D switching operation section 53, the control section 631 acquires characteristic information relating to the brightness of the 3D monitor 5 from the ID memory 5a, and controls the light adjustment detection section 635, based on the characteristic information.

<Action of Eighth Embodiment>

Next, action of the endoscope system according to the eighth embodiment is described.

The control section 631 confirms the operation state of the 2D/3D switching operation section 53. When the 2D outputting mode is selected, the control section 631 controls the 2D/3D image signal switching section 54 and the light adjustment detection section 635, as with the above-described seventh embodiment.

On the other hand, when the 3D outputting mode is selected in the confirmation of the operation state of the 2D/3D switching operation section 53, the control section 631 controls and switches the 2D/3D image signal switching section 54 to use the first image pickup signal outputted from the first signal processing section 32 as the 3D composing signal, and acquires the characteristic information relating to the brightness of the 3D monitor 5 from the ID memory 5a, thereby controlling the light adjustment detection section 635, based on the characteristic information.

As described above, when the 3D outputting mode is selected, the endoscope system according to the eighth embodiment acquires the characteristic information relating to the brightness of the 3D monitor connected to the processor and controls the brightness (the luminance value) of the object image to be picked up, based on the characteristic information. This makes it possible to secure brightness similar to the brightness in the 2D observation more accurately even if the dedicated 3D eyewear is worn in the 3D observation.

<Ninth Embodiment>

Next, a ninth embodiment of the present invention is described with reference to FIG. 12.

Figure 12:
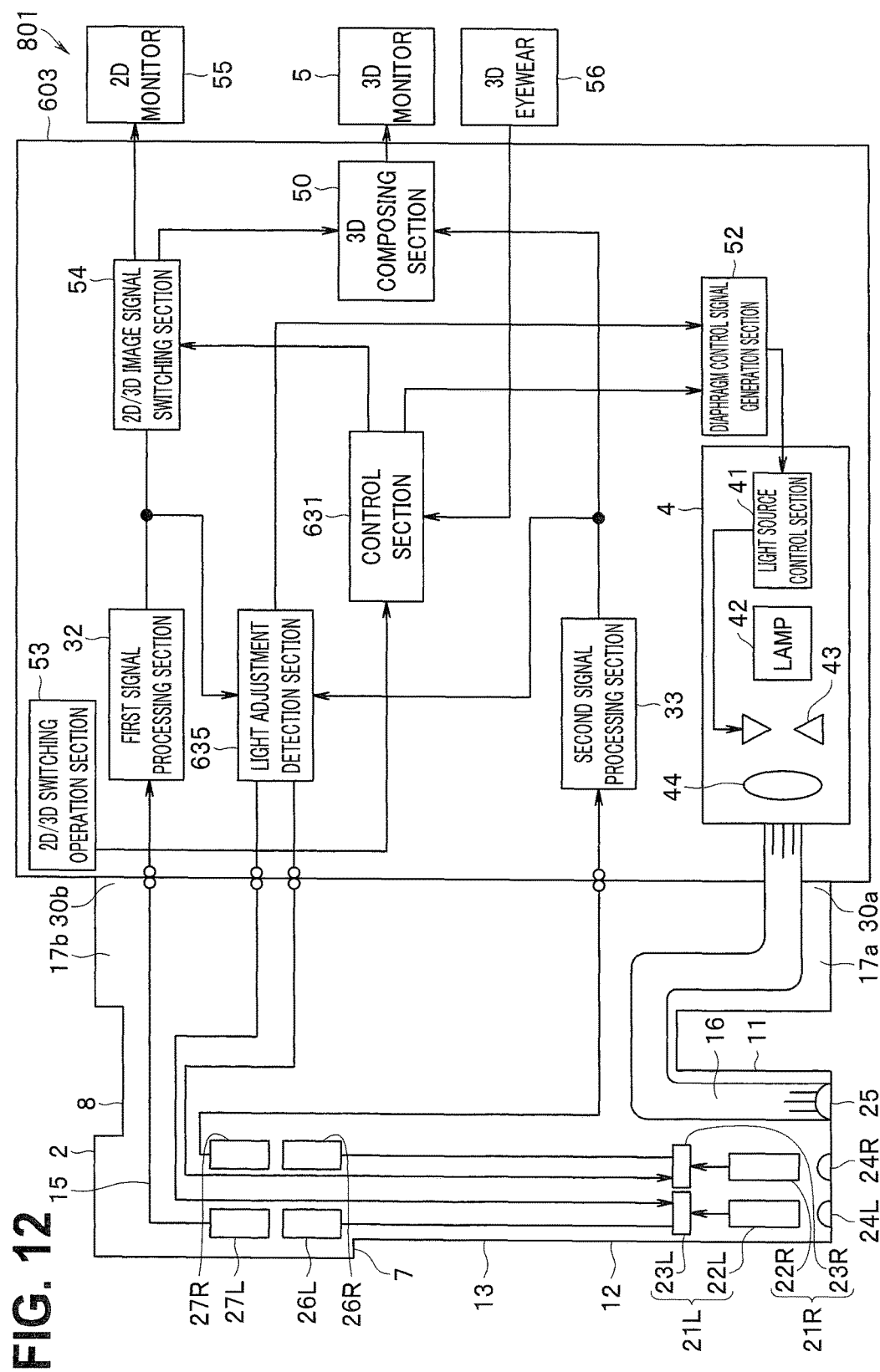
FIG. 12 is a block diagram illustrating a configuration of an endoscope system according to a ninth embodiment of the present invention.

As illustrated in FIG. 12, an endoscope system 801 according to the ninth embodiment is an endoscope system that has a basic configuration similar to the endoscope system 601 of the seventh embodiment, and picks up an image with use of the stereoscopic endoscope 2 as with the first and second embodiments. The endoscope system 801 includes a switching mechanism of 2D and 3D and reproduces a 2D image on the 2D monitor in addition to display of a 3D image on the 3D monitor.

Further, in the ninth embodiment, brightness of the object image to be picked up is adjusted according to specification of the dedicated eyewear used in the 3D observation. The other components and action are similar to the components and the action of the seventh and eighth embodiments. Therefore, only difference with the seventh and eighth embodiments is described, and the detailed description of the components and the action similar to the components and the action of the seventh and eighth embodiments is omitted.

As illustrated in FIG. 12, the processor 603 according to the ninth embodiment has a configuration similar to the configuration of the processor according to the seventh embodiment; however, the control section 631 acquires specification information of a dedicated eyewear 56 used in the 3D observation. The dedicated eyewear 56 is connected to the processor 603. In the ninth embodiment, when the 3D outputting mode is selected by the 2D/3D switching operation section 53, the control section 631 acquires the predetermined specification information from the eyewear 56, and controls the light adjustment detection section 635, based on the specification information.

<Action of Ninth Embodiment>

Next, action of the endoscope system according to the ninth embodiment is described.

The control section 631 confirms the operation state of the 2D/3D switching operation section 53. When the 2D outputting mode is selected, the control section 631 controls the 2D/3D image signal switching section 54 and the light adjustment detection section 635, as with the above-described seventh embodiment.

On the other hand, when the 3D outputting mode is selected in the confirmation of the operation state of the 2D/3D switching operation section 53, the control section 631 controls and switches the 2D/3D image signal switching section 54 to use the first image pickup signal outputted from the first signal processing section 32 as the 3D composing signal, and acquires the predetermined specification information from the dedicated 3D eyewear 56, thereby controlling the light adjustment detection section 635, based on the specification information.

As described above, when the 3D outputting mode is selected, the endoscope system according to the ninth embodiment acquires the specification information relating to the dedicated eyewear 56 used in the 3D observation and controls the brightness (the luminance value) of the object image to be picked up, based on the specification information. This makes it possible to secure brightness similar to the brightness in the 2D observation more accurately even if the dedicated 3D eyewear is worn in the 3D observation.

Note that, in the seventh to ninth embodiments, the brightness (the luminance value) of the object image is automatically adjusted when the observation mode is switched from the 2D observation mode to the 3D observation mode; however, the adjustment is not limited to the brightness, and color (the color tone or the gradation) of the image signal may be automatically adjusted.

In addition, in the seventh to ninth embodiments, the brightness (the luminance value) of the object image is automatically adjusted when the observation mode is switched from the 2D observation mode to the 3D observation mode in response to the switching operation of the 2D/3D switching operation section 53, in the observation of the object image. The adjustment, however, is not limited to the above description, and the brightness may be automatically adjusted according to whether a recording mode is a 2D recording mode or a 3D recording mode in recording of the picked-up object image.

The present invention is not limited to the above-described embodiments, and various modifications and alterations are possible without departing from the scope of the invention.

What is claimed is:

1. An image pickup system comprising:
a first stereoscopic endoscope comprising:
   a first image pickup device configured to pick up a first optical image of an object and a first image pickup signal based on the first optical image;
   a second image pickup device configured to pick up a second optical image of the object having parallax with respect to the first optical image, and output a second image pickup signal based on the first optical image; and
   a memory configured to store a difference correction parameter indicating information on a difference between a characteristic of the first image pickup device and a characteristic of the second image pickup device; and
a processor comprising hardware, wherein the processor is configured to:
   selectively connect to:
      the first stereoscopic endoscope to receive the first image pickup signal output by the first image pickup device, the second image pickup signal output by the second image pickup device, and the difference correction parameter stored by the memory; and
      a second stereoscopic endoscope to receive other image pickup signals for processing; and
   perform correction processing on at least one of the first image pickup signal and the second image pickup signal received from the first stereoscopic endoscope based on the difference correction parameter to reduce an effect of the difference between the characteristic of the first image pickup device and the characteristic of the second image pickup device on the first image pickup signal and the second image pickup signal.

2. The image pickup system according to claim 1, wherein the difference correction parameter stored in the memory comprises:
   first correction parameter indicating information on a sensitivity characteristic of the first image pickup device; and
   a second correction parameter indicating information on a sensitivity characteristic of the second image pickup device, and
wherein the processor is configured to perform the correction processing on the first image pickup signal based on the first correction parameter and on the second image pickup signal based on the second correction parameter to reduce the effect caused by the difference between the sensitivity characteristic of the first image pickup device and the sensitivity characteristic on the second image pickup device on the first image pickup signal and the second image pickup signal.

3. The image pickup system according to claim 1, wherein the difference correction parameter indicates correction information on a difference between an image characteristic expressed by the first image pickup signal and an image characteristic expressed by the second image pickup signal, and
wherein the processor is configured to perform the correction processing on at least one of the first image pickup signal and the second image pickup signal based on the difference correction parameter to reduce the effect caused by the difference between the image characteristic expressed by the first image pickup signal and the image characteristic expressed by the second image pickup signal.

4. The image pickup system according to claim 1, wherein the processor is configured to:
   perform image processing on the first image pickup signal and the second image pickup signal; and
   detect brightness of the optical image of the object expressed by one of the first image pickup signal and the second image pickup signal subjected to the image processing and subjected to the correction processing.

5. The image pickup system according to claim 1, wherein the difference correction parameter indicates luminance level correction information on a difference between a luminance level of a first image expressed by the first image pickup signal and a luminance level of a second image expressed by the second image pickup signal, and
wherein the processor is configured to perform the correction processing on at least one of the first image pickup signal and the second image pickup signal based on the difference correction parameter to reduce the effect caused by the difference between the luminance level of the first image expressed by the first image pickup signal and the luminance level of the second image expressed by the second image pickup signal.

6. The image pickup system according to claim 1, wherein the difference correction parameter indicates gradation correction information on a difference between a gradation characteristic of one or more pixels of the first image pickup device and a gradation characteristic of one or more pixels of the second image pickup device, and
wherein the processor is configured to perform the correction processing on at least one of the first image pickup signal and the second image pickup signal received from the first stereoscopic endoscope based on the difference correction parameter to reduce an effect of the difference between the gradation characteristic of the one or more pixels of the first image pickup device and the gradation characteristic of the one or more pixels of the second image pickup device on the first image pickup signal and the second image pickup signal.

7. The image pickup system according to claim 1, wherein the difference correction parameter indicates color tone correction information one a difference between a color tone of one or more pixels of the first image pickup device and a color tone characteristic of one or more pixels of the second image pickup device, and
wherein the processor is configured to perform the correction processing on at least one of the first image pickup signal and the second image pickup signal received from the first stereoscopic endoscope based on the difference correction parameter to reduce an effect of the difference between the color tone of the one or more pixels of the first image pickup device and the color tone characteristic of the one or more pixels of the second image pickup device on the first image pickup signal and the second image pickup signal.

8. The image pickup system according to claim 1,
wherein the processor is configured to compose the first image pickup signal and the second image pickup signal to generate a stereoscopic image,
wherein the difference correction parameter indicates eccentricity correction information on the difference between the characteristic of the first image pickup device and the characteristic of the second image pickup device that cause a parallax of the stereoscopic image generated to be different from a predetermined parallax, and
wherein the processor is configured to perform the correction processing on at least one of the first image pickup signal and the second image pickup signal based on the difference correction parameter to cause the parallax of the stereoscopic image generated to approach the predetermined parallax.

9. The image pickup system according to claim 1,
wherein the difference correction parameter indicates white spot correction information on the difference between the characteristic of the first image pickup device caused by one or more white spot pixels of the first image pickup device and the characteristic of the second image pickup device caused by one or more white spot pixels of the second image pickup device, and
wherein the processor is configured to perform the correction processing on the at least one of the first image pickup signal and the second image pickup signal based on the difference correction parameter to reduce an effect caused by the one or more white spot pixels of the first image pickup device, the one or more white spot pixels of the second image pickup device, or both.

10. An image pickup system comprising:
a processor comprising hardware, wherein the processor is configured to:
selectively connect to:
a first stereoscopic endoscope to receive:
a first image pickup signal output by a first image pickup device of the first stereoscopic endoscope based on a first optical image picked up by the first image pickup device;
a second image pickup signal output by a second image pickup device of the first stereoscopic endoscope based on a second optical image picked up by the second image pickup device; and
a difference correction parameter stored by a memory of the first stereoscopic endoscope, the difference correction parameter indicating information on a difference between a characteristic of the first image pickup device and a characteristic of the second image pickup device; and
a second stereoscopic endoscope to receive other image pickup signals for processing; and
perform correction processing on at least one of the first image pickup signal and the second image pickup signal received from the first stereoscopic endoscope based on the difference correction parameter to reduce an effect caused by the difference between the characteristic of the first image pickup device and the characteristic of the second image pickup device on the first image pickup signal and the second image pickup signal.

* * * * *